(12) United States Patent
Shahmohammadi et al.

(10) Patent No.: US 10,656,710 B1
(45) Date of Patent: *May 19, 2020

(54) APPARATUS, SYSTEMS, AND METHODS FOR SENSING BIOPOTENTIAL SIGNALS VIA COMPLIANT ELECTRODES

(71) Applicant: Facebook Technologies, LLC, Menlo Park, CA (US)

(72) Inventors: Mohsen Shahmohammadi, Pittsburgh, PA (US); Ying Yang, Pittsburgh, PA (US); Yaser Sheikh, Pittsburgh, PA (US); Hernan Badino, Pittsburgh, PA (US); James David White, Pittsburgh, PA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/036,528

(22) Filed: Jul. 16, 2018

(51) Int. Cl.
*G06F 3/01* (2006.01)
*G06F 1/16* (2006.01)
*G02B 27/01* (2006.01)

(52) U.S. Cl.
CPC ......... *G06F 3/015* (2013.01); *G02B 27/0176* (2013.01); *G06F 1/163* (2013.01); *G06F 1/1637* (2013.01); *G06F 1/1656* (2013.01); *G06F 3/013* (2013.01); *G06F 3/017* (2013.01); *G02B 2027/0178* (2013.01)

(58) Field of Classification Search
None
See application file for complete search history.

(56) References Cited

U.S. PATENT DOCUMENTS

2008/0137909 A1* 6/2008 Lee .................. A61B 3/113
  382/103
2018/0348863 A1* 12/2018 Aimone ............... G06F 3/011

OTHER PUBLICATIONS

Seyedi et al., "Effect of Limb Joints and Limb Movement on Intrabody Communications for Body Area Network Applications" Journal of Medical and Biological Engineering, vol. 34, No. 3, 2014, pp. 276-283.
Worgan et al., "PowerShake: Power Transfer Interactions for Mobile Devices" https://dl.acm.org/citation.cfm?doid=2858036.2858569, 1 page.

(Continued)

*Primary Examiner* — Duane N Taylor, Jr.
(74) *Attorney, Agent, or Firm* — FisherBroyles, LLP

(57) ABSTRACT

An interactive system may include (1) a facial coupling subsystem configured to conduct a biopotential signal generated by a user's body, (2) a receiving subsystem electrically connected to the facial coupling subsystem and configured to receive, from the user's body via a compliant electrode of the facial coupling subsystem, the biopotential signal, and (3) a detection subsystem electrically connected to the receiving subsystem and configured to (a) determine a characteristic of the biopotential signal and (b) use the characteristic of the biopotential signal to determine a gaze direction of an eye of the user and/or a facial gesture of the user. In some examples, the facial coupling subsystem may include a plurality of compliant electrodes that each are configured to comply in a direction normal to a surface of the user's face. Various other apparatus, systems, and methods are also disclosed.

20 Claims, 27 Drawing Sheets

(56) References Cited

OTHER PUBLICATIONS

Zhang et al., "TouchPower: Interaction-based Power Transfer for Power-as-needed Devices" https://dl.acm.org/citation.cfm?doid=3139486.3130986, 1 page.
Li et al., "Characterization of the implantable intra-body communication based on capacitive coupling by transfer function" https://ieeexplore.ieee.org/document/7796259/, 2 pages.
Cohn et al., "An ultra-low-power human body motion sensor using static electric field sensing" https://dl.acm.org/citation.cfm?doid=2370216.2370233, 1 page.
Glass https://www.x.company/glass/, 3 pages.
Introducing the Vuzix Blade® AR Smart Glasses https://www.vuzix.com/products/blade-smart-glasses, 1 page.
Google and Novartis Ink Deal for smart Contact Lenses http://thetechielifestyle.blogspot.com/2014/07/google-and-novartis-ink-deal-for-smart.html, 3 page.
"The Mobile Future of Augmented Reality" Qualcomm Technologies, Inc. Dec. 2016, 39 pages.
"VR and AR pushing connectivity limits" Qualcomm Technologies, Inc. May 2017, 24 pages.
Mazloum. Nafiseh Seyed,"Body-Coupled Communications Experimental characterization, channel modeling and physical layer design" Dec. 2008, 120 pages.
Wegmueller et al., "Signal Transmission by Galvanic Coupling Through the Human Body" https://ieeexplore.ieee.org/document/5280245/ 1 page.
Ensworth et al., "Every smart phone is a backscatter reader: Modulated Backscatter compatibility with Bluetooth 4.0 Low Energy (BLE) Devices" https://ieeexplore.ieee.org/document/7113076/ 1 page.
Yang et al., "Riding the airways: Ultra-wideband ambient backscatter via commercial broadcast systems" https://ieeexplore.ieee.org/document/8057162/.
Post et al., "Intrabody Buses for Data and Power" 4 pages.
Zhang et al., "Enabling Practical Backscatter Communication for On-body Sensors" 14 pages.
Zimmerman. Guthrie Thomas., "Personal Area Networks (PAN): Near-Field Intra-Body Communication" 81 pages.
Zhang et al., "Modeling and Characterization of the Implant Intra-Body Communication Based on Capacitive Coupling Using a Transfer Function Method" Sensors 2014,vol. 14, pp. 1740-1756.
Researchers Jins Memel, https://jins-meme.com/en/researchers/ p. 1.
Murtaza Dhuliawala et al. 'Research Examples' vastly-Expanding World With Jins Meme https://jins-meme.com/en/researchers/casestudies/ 1 page.
De Luca "The Use of Surface Electromyography in Biomechanics" Journal of Applied Biomechanics, 1997,vol. 13, pp. 135-163.
Products—Wearable Sensing http://wearablesensing.com/all-products/ p. 1.
Reach Bionics Awakening Human Potential Conjure facial Expression VR Controller, https://www.reachbionics.com/conjure- p. 1.
Hands-free VR interface monitors facial Expressions http://www.eenewseurope.com/news/hands-free-vr-interface-monitors-facial-expressions p. 1.
OpenBCI http://openbci.com/community/wavr-brainwave-meets-vr/, 1 page.
Homepage—Emotiv https://www.emotiv.com/ 1 page.
Hetter. P Gregory, "Corneal-Retinal Potential Behind Closed Eye-lids" 1 page.
The Electric Signals Originating in the eye http://www.bem.fi_book_28_28.htm, 1 page.
Jou et al., "Towards Continuous Speech Recognition Using Surface Electromyography" INTERSPEECH 2006—ICSLP, 4 pages.
Chi et al., "Wireless Non-contact EEG/ECG Electrodes for Body Sensor Networks" 1 page.
A system for active compensation of motion artifacts in non-contact ECG sensing https://lifesciences.ieee.org_life, 1 page.
Hexoskin Smart Shirts Garment Specifications—Cardiac, Respiratory https://www.hexoskin.com, 1 page.
Conductive Garment Elbow Sleeve https://www.alimed.com_sleeve-conductive-fabric html, p. 1.
Technology to Measure Human Emotion in the Real World, Emteq https://emteq.net, 1 page.
Inmersys I Virtual Reality and Augmented Reality https://www.inmersys.com/en/home, p. 1.
Imec and Holst Centre introduce EEG Headset for Emotion Detection https://www.imec-int.com/en/articles/imec-and-holst-centre-introduce-eeg-headset-for-emotion-detection, 1 page.
Iooxid labs helps a better Understanding of Unspoken Emotion Using Human Physiological signal Explore User Mind http://Iooxidlabs.com/, 1 page.

\* cited by examiner

FIG. 17A  FIG. 17B

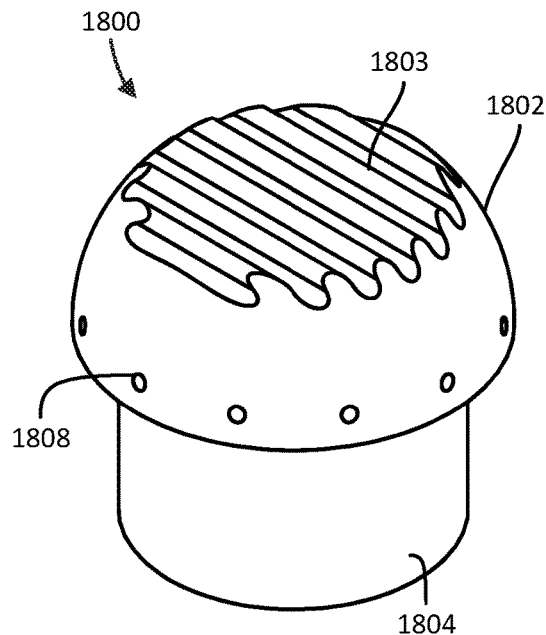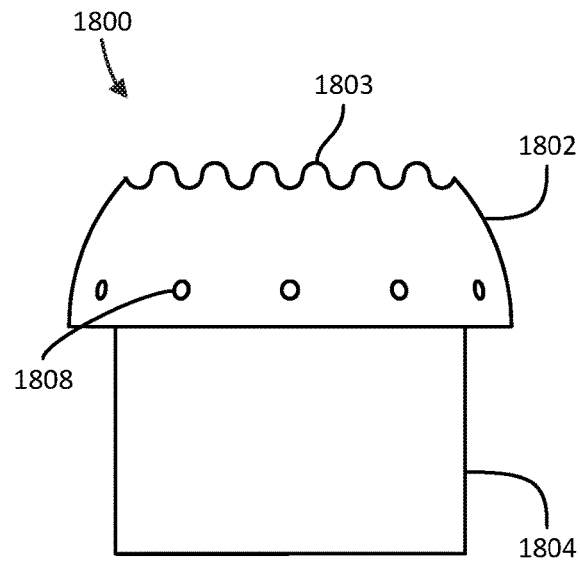
*FIG. 18A*
*FIG. 18B*
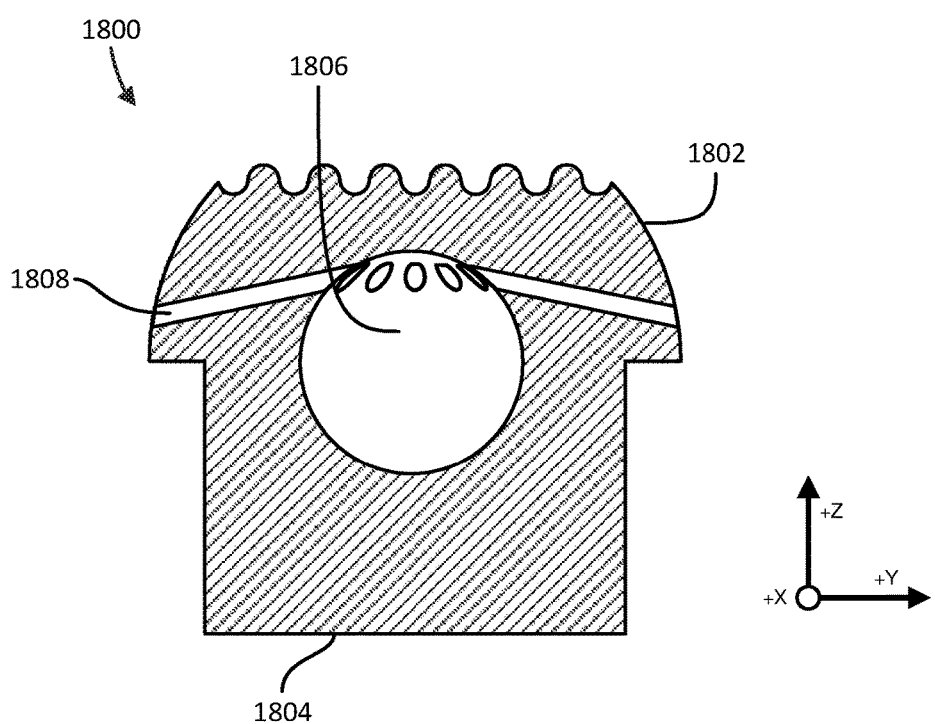
*FIG. 18C*

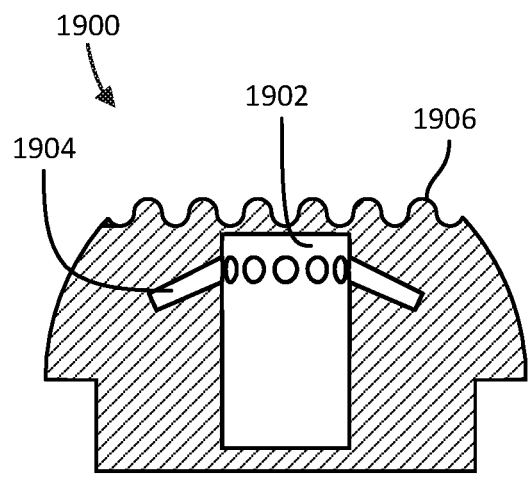
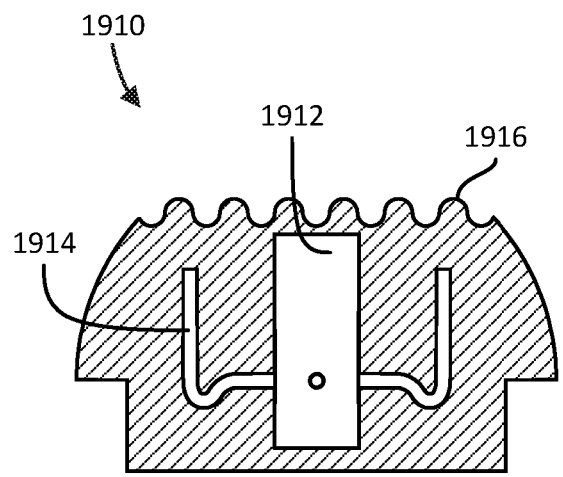
FIG. 19A
FIG. 19B
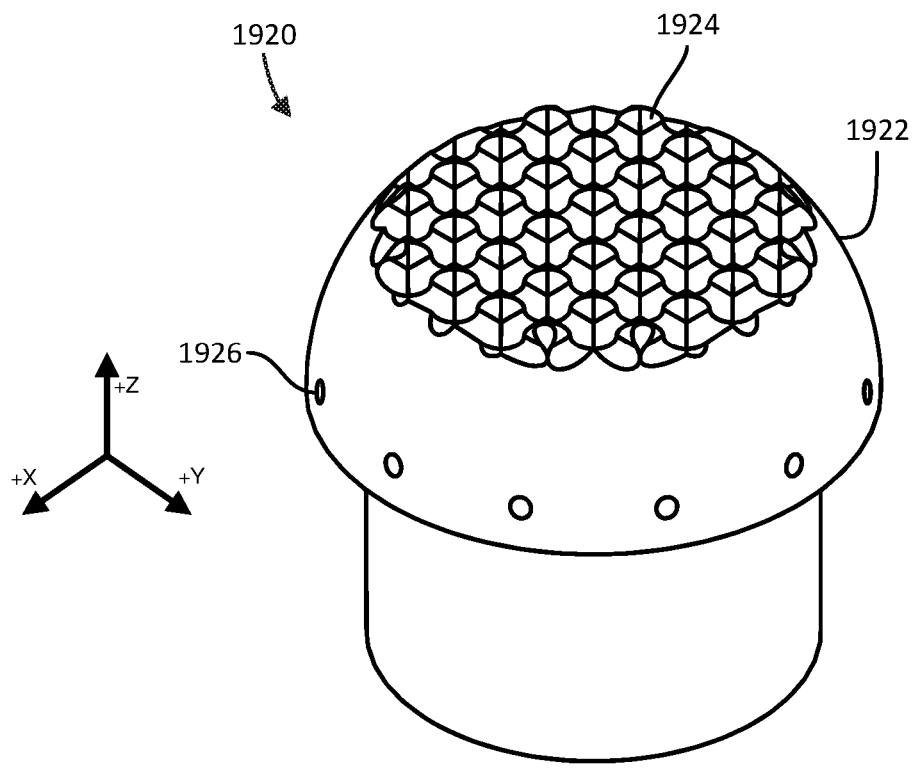
FIG. 19C

APPARATUS, SYSTEMS, AND METHODS FOR SENSING BIOPOTENTIAL SIGNALS VIA COMPLIANT ELECTRODES

BACKGROUND

The disclosure relates generally to wearable devices, and more specifically to head-mounted-display devices and systems.

Virtual reality (VR) and augmented reality (AR) headsets are gaining in popularity for use in a growing number of activities. Such headsets may integrate visual information into a user's field of view to enhance their surroundings or allow them to step into immersive three-dimensional environments. While virtual reality and augmented reality headsets are often utilized for gaming and other entertainment purposes, they are also commonly employed for purposes outside of recreation—for example, governments may use them for military training simulations, doctors may use them to practice surgery, and engineers may use them as visualization aids. Virtual and augmented reality systems are also increasingly recognized for their utility in facilitating interpersonal interactions between individuals in a variety of contexts.

Head-mounted devices, such as AR and VR headsets, typically need to be light in weight and have small profiles. Accordingly, physical interfaces allowing for input of user commands are often limited in these head-mounted devices and may only permit a select number of inputs by users. Unfortunately, inputting more complex user commands may be challenging due to these interface constraints. Additionally, while AR and VR headsets are increasingly utilized in remote interactions between users, a user's eyes and facial movements may be partially or fully obscured when wearing such headsets. As such, users of conventional headsets are typically unable to exchange more nuanced body-language cues, such as user facial expressions and/or gaze directions. The instant disclosure, therefore, identifies and addresses a need for apparatus, systems, and methods for facilitating interactions between users and wearable devices and/or between users of wearable devices, especially VR and AR headsets.

SUMMARY

As will be described in greater detail below, the instant disclosure describes various apparatus, systems, and methods for facilitating user interaction with electronic devices and interactions between users of electronic devices. In one example, an interactive system (e.g., a head-mounted-display device) may include (1) a facial coupling subsystem configured to conduct a biopotential signal (e.g., an Electrooculography (EOG) signal or an Electromyography (EMG) signal) generated by a user's body, (2) a receiving subsystem electrically connected to the facial coupling subsystem and configured to receive, from the user's body via a compliant electrode of the facial coupling subsystem, the biopotential signal, and (3) a detection subsystem electrically connected to the receiving subsystem and configured to (a) determine a characteristic of the biopotential signal and (b) use the characteristic of the biopotential signal to determine a gaze direction of an eye of the user and/or a facial gesture of the user. In some examples, the facial coupling subsystem may include (1) a compliant cushion layer with (a) a user-side surface dimensioned to abut a facial portion of the user and (b) a display-side surface dimensioned to abut a mounting surface of a head-mounted device and/or (2) a plurality of compliant electrodes that each are configured to comply in a direction normal to a surface of the user's face.

In some examples, each of the plurality of compliant electrodes may be further configured to substantially resist motion in any direction tangent to the surface of the user's face. In at least one example, each of the plurality of compliant electrodes may include an interface mateable to an opposing interface of the mounting surface of the head-mounted device, and the interface of each of the plurality of compliant electrodes may be configured to allow the compliant electrode to move in the direction normal to the surface of the user's face and substantially prevent the compliant electrode from moving in any direction tangent to the surface of the user's face.

In some examples, the interface of each of the plurality of compliant electrodes may include a plurality of legs, and each of the plurality of legs may be mateable to an opposing socket of the mounting surface of the head-mounted device. In other examples, the interface of each of the plurality of compliant electrodes may include a plurality of sockets, and each of the plurality of sockets may be mateable to an opposing leg of the mounting surface of the head-mounted device. In at least one example, the interface of each of the plurality of compliant electrodes may include a tubular housing mateable to an opposing tubular socket of the mounting surface of the head-mounted device.

In some examples, each of the plurality of compliant electrodes may include compliant foam configured to apply a force against the compliant electrode and the mounting surface of the head-mounted device when the compliant electrode is compressed by the surface of the user's face. In some examples, each of the plurality of compliant electrodes may include a spring configured to apply a force against the compliant electrode and the mounting surface of the head-mounted device when the compliant electrode is compressed by the surface of the user's face.

In some examples, each of the plurality of compliant electrodes may be composed of a single piece of conductive polymer. In some examples, the single piece of conductive polymer may include a hollow center configured to enable the single piece of conductive polymer to comply in the direction normal to the surface of the user's face and substantially resist motion in any direction tangent to the surface of the user's face. In at least one example, the single piece of conductive polymer may include a plurality of openings configured to enable air to flow to and from the hollow center.

In some examples, the single piece of conductive polymer may include (1) a user-side surface with a first rigid metallic conductor configured to contact the surface of the user's face and (2) a display-side surface with a second rigid metallic conductor configured to conduct the biopotential signal to electronic components of the head-mounted device. In such examples, the hollow center may be filled by a conductive liquid that electrically connects the first rigid metallic conductor to the second rigid metallic conductor.

In various examples, the single piece of conductive polymer may include a spherical user-side surface, a flat user-side surface, or a user-side surface with ridges or equally spaced protrusions. In at least one example, the interactive system may further include a communication subsystem configured to transmit data to an external device. The communication subsystem may also be configured to modify the data transmitted to the external device based on the gaze direction or the facial gesture.

A corresponding head-mounted-display device may include (1) a facial coupling subsystem configured to conduct a biopotential signal generated by a user's body, (2) a receiving subsystem electrically connected to the facial coupling subsystem and configured to receive, from the user's body via a compliant electrode of the facial coupling subsystem, the biopotential signal, and (3) a detection subsystem electrically connected to the receiving subsystem and configured to determine a characteristic of the biopotential signal and use the characteristic of the biopotential signal to determine a gaze direction of an eye of the user and/or a facial gesture of the user. In some examples, the facial coupling subsystem may include (1) a compliant cushion layer with (a) a user-side surface dimensioned to abut a facial portion of the user and (b) a display-side surface dimensioned to abut a mounting surface of a head-mounted device and/or (2) a plurality of compliant electrodes that each are configured to comply in a direction normal to a surface of the user's face. In some examples, the head-mounted-display device may further include (1) a display region configured to display images to the user and (2) a display controller configured to modify the images displayed in the display region based on the gaze direction of the user's eye or the facial gesture of the user.

A corresponding method may include (1) receiving, from a user's body via a compliant electrode of a head-mounted display device, a biopotential signal, (2) determining a characteristic of the biopotential signal, and (3) using the characteristic of the biopotential signal to determine a gaze direction of an eye of the user and/or a facial gesture of the user. In some examples, the compliant electrode may be configured to comply in a direction normal to a surface of the user's face, and the biopotential signal may be generated by a corneo-retinal electric potential that exists between a front and a back of the user's eye and/or an electric potential of a muscle of the user.

Features from any of the above-mentioned embodiments may be used in combination with one another in accordance with the general principles described herein. These and other embodiments, features, and advantages will be more fully understood upon reading the following detailed description in conjunction with the accompanying drawings and claims.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

FIGS. 17A-17C are a perspective view, a side view, and a cross-sectional view of an additional exemplary compliant electrode in accordance with some embodiments.

FIGS. 18A-18C are a perspective view, a side view, and a cross-sectional view of an additional exemplary compliant electrode in accordance with some embodiments.

FIG. 19A is a cross-sectional view of an additional exemplary compliant electrode in accordance with some embodiments.

FIG. 19B is a cross-sectional view of an additional exemplary compliant electrode in accordance with some embodiments.

FIG. 19C is a perspective view of an additional exemplary compliant electrode in accordance with some embodiments.

Figure 1A:
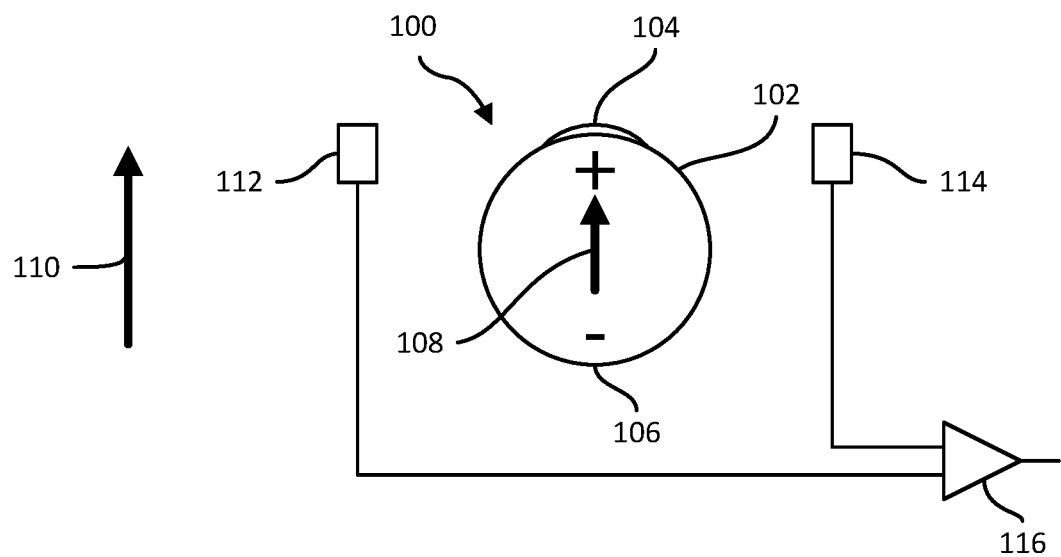
FIGS. 1A and 1B are diagrams of an exemplary biopotential-signal source in accordance with some embodiments.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION OF EXEMPLARY EMBODIMENTS

The present disclosure is generally directed to apparatus, systems, and methods for using biopotential signals generated by users' bodies and conducted by compliant electrodes to facilitate user interactions with electronic devices and/or interactions between users of electronic devices. As will be explained in greater detail below, embodiments of the instant disclosure may enable a head-mounted device, such as a head-mounted display, with integrated compliant electrodes to harness biopotential signals generated by a wearer's body to detect the wearer's facial movements. By using compliant electrodes that comply in a direction normal to a wearer's face while restricting motion in any direction tangent to the wearer's face, embodiments of the instant disclosure may accurately and reliably measure biopotential signals generated by the wearer's body in a way that is also comfortable to the wearer.

In some examples, by accurately and reliably monitoring biopotential signals generated by a wearer's facial muscles and/or eyes, embodiments of the instant disclosure may enable devices to track the wearer's facial gestures and/or gaze direction based on changes in various characteristics of these biopotential signals. Such apparatus, systems, and methods may enable user interaction with electronic devices, such as head-mounted displays, without requiring users to input operations via conventional input interfaces, such as keyboards, controllers, headset buttons, voice-command interfaces, etc. Detection of user facial movements using biopotential-signal sensing may require less energy than conventional optical methods, thereby reducing power use and extending the life of battery-operated devices. Moreover, users may easily and efficiently convey facial movements to other remote users via such apparatus, systems, and methods. Accordingly, users may interact with electronic devices and other users in a manner that provides a broader range of interactive capabilities while facilitating a greater sense of immersion in VR and AR environments.

Figure 1B:
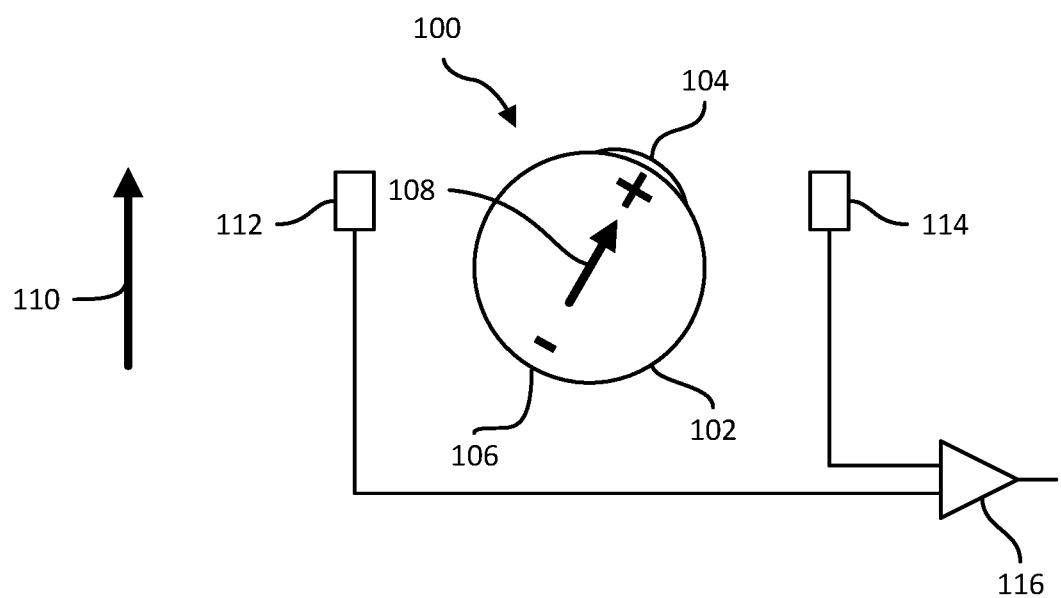
Figure 2:
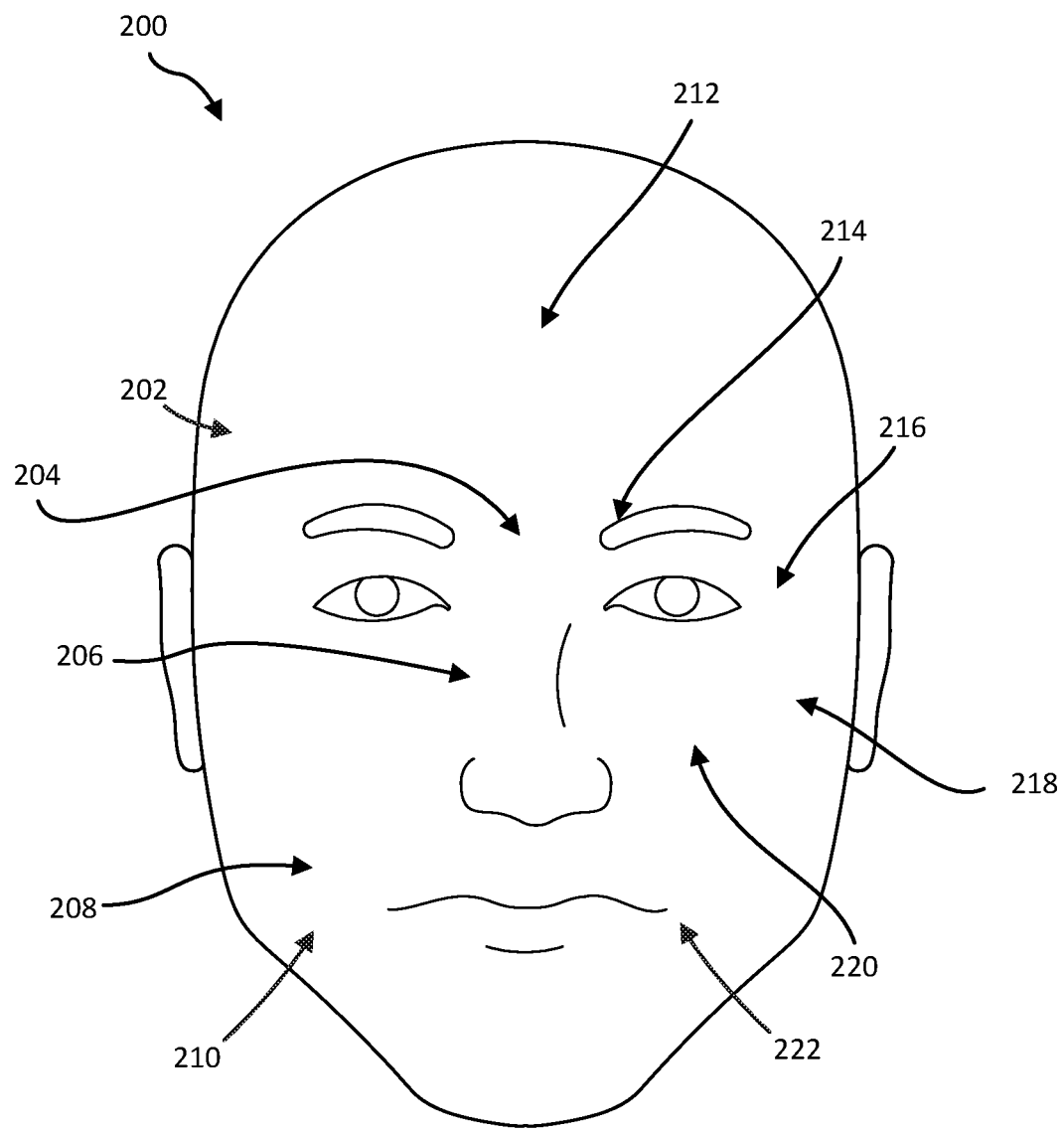
FIG. 2 is a diagram of additional exemplary biopotential-signal sources in accordance with some embodiments.

The following will provide, with reference to FIGS. 1 and 2, examples sources of biopotential signals. The descriptions corresponding to FIGS. 3-22, will provide examples of systems and devices for using biopotential signals acquired using compliant electrodes to facilitate user interaction with electronic devices and/or interaction between users of electronic devices. Further, the discussion corresponding to FIG. 23 will provide examples of methods for using biopotential signals to facilitate user interaction with electronic devices and/or interaction between users of electronic devices. In addition, the discussion corresponding to FIGS. 24, 25A-25F, 26A-26F, and 27A-27C will provide examples of facial movements and gestures that may be detected by the disclosed devices and systems.

FIGS. 1A, 1B, and 2 illustrate exemplary sources of biopotential signals that may be harnessed by the systems described herein to facilitate user interaction with electronic devices and/or interactions between users of electronic devices. In some examples, the term "biopotential signal" may refer to any oscillating or alternating electric-potential signal that is generated by a user's body and that may be measured across two compliant electrodes connected to or in close proximity to the user's body. Examples of biopotential signals include, without limitation, EOG signals generated by movements of a user's eyes and EMG signals generated by a user's muscles.

FIGS. 1A and 1B show a corneo-retinal electric potential 100 of a user's eye 102 that may generate an EOG signal that is measurable by the systems described herein. As shown in these figures, corneo-retinal electric potential 100 may exist between a cornea 104 and a retina 106 of eye 102. As a result of corneo-retinal electric potential 100, eye 102 may act as a dipole in which cornea 104 acts as the dipole's positive pole and retina 106 acts as the dipole's negative pole. As shown in FIGS. 1A and 1B, corneo-retinal electric potential 100 may be aligned with a gaze direction 108 of eye 102. When the user looks straight ahead, corneo-retinal electric potential 100 and gaze direction 108 of eye 102 may align with a head direction 110 of the user, as shown in FIG. 1A. Alternatively, when the user looks right, left, up, or down, corneo-retinal electric potential 100 and gaze direction 108 of eye 102 may diverge with head direction 110, as shown in FIG. 1B. In some examples, corneo-retinal electric potential 100 may induce a biopotential signal across compliant electrodes 112 and 114 that may be measured by biopotential-sensing circuitry 116. This biopotential signal may trend more positive or more negative depending on gaze direction 108. Using FIGS. 1A and 1B as an example, as gaze direction 108 moves from that shown in FIG. 1A to that shown in FIG. 1B, the biopotential signal measured by compliant electrode 112 may trend more negative while the biopotential signal measured by compliant electrode 114 may trend more positive, which may indicate that gaze direction 108 is moving away from compliant electrode 112 and towards compliant electrode 114.

FIG. 2 shows various facial muscles of a user's face 200 that may generate EMG signals when they are activated or engaged to make a particular facial expression (e.g., a smile, a frown, etc.). Varying levels of activation or engagement of these muscles may generate varying electric potentials and thus measurable biopotential signals. Examples of facial muscles that may generate biopotential signals include, without limitation, a temporoparietalis muscle 202, a procerus muscle 204, a nasalis muscle 206, a buccinator muscle 208, a risorius muscle 210, a frontalis muscle 212, a corrugator supercilii muscle 214, an orbicularis oculi muscle 216, a zygomaticus major muscle 218, a levator labii superioris muscle 220, and an orbicularis oris muscle 222.

Figure 3:
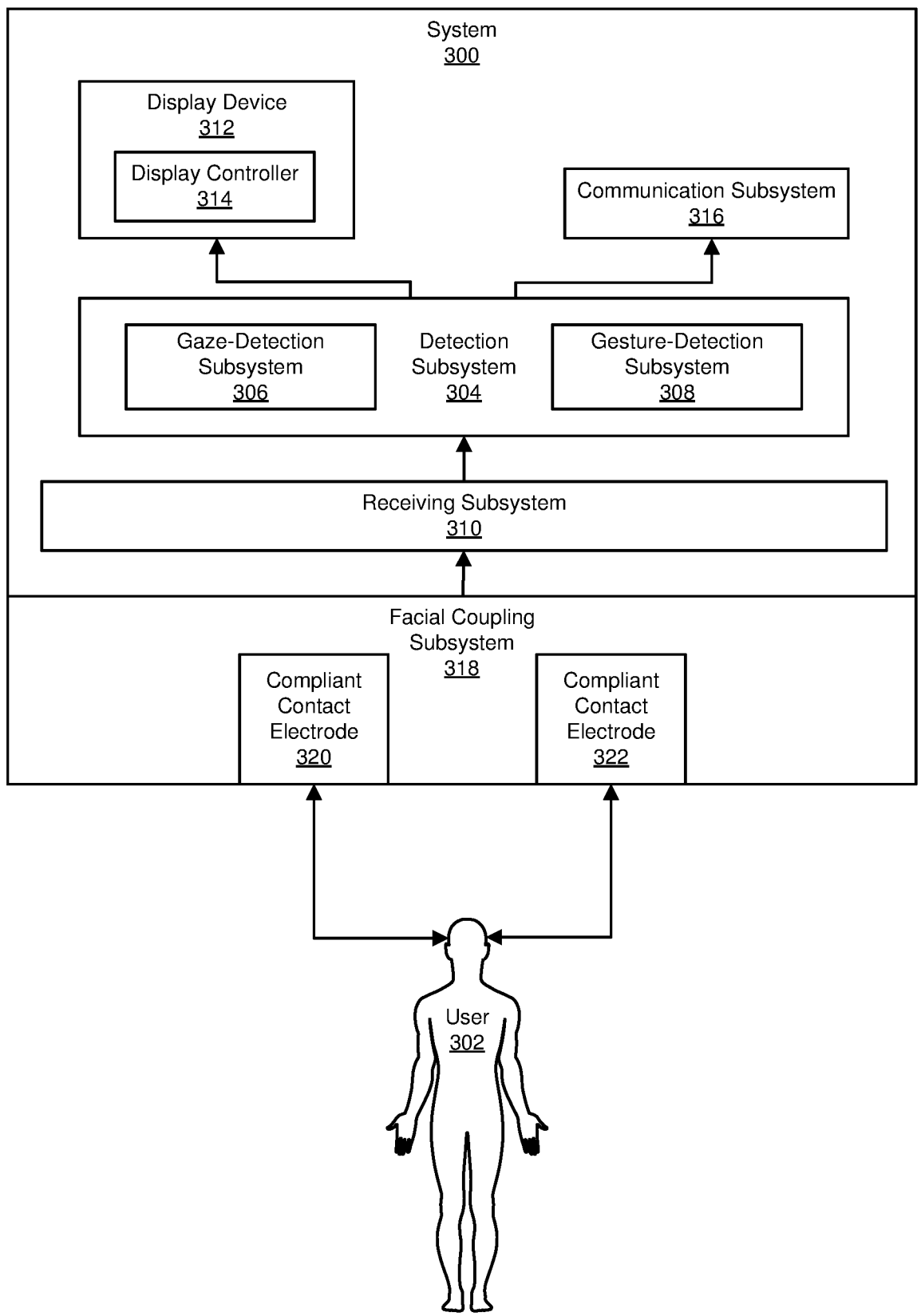
FIG. 3 is a block diagram of an exemplary galvanically coupled interactive system in accordance with some embodiments.
Figure 4:
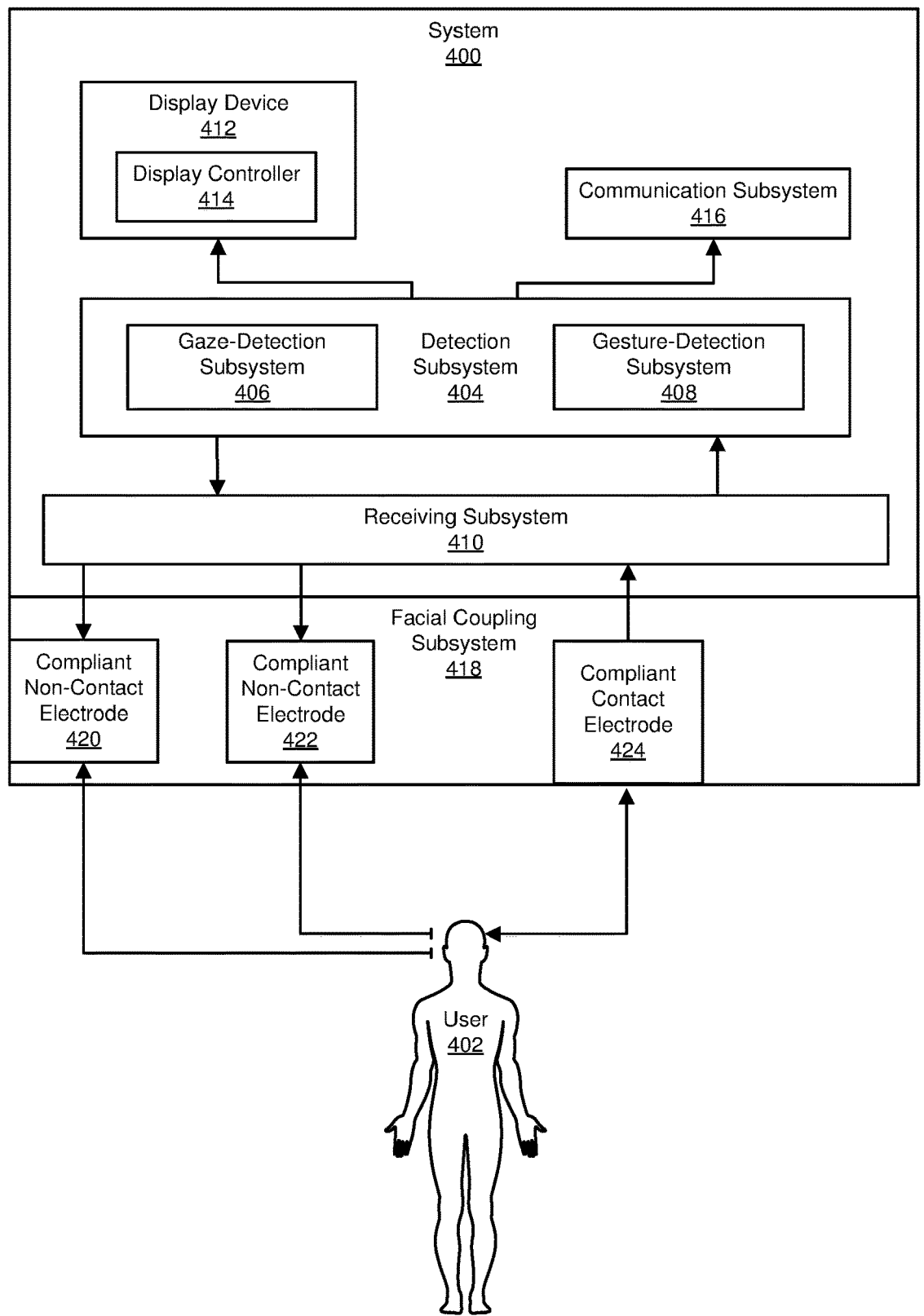
FIG. 4 is a block diagram of an exemplary capacitively coupled interactive system in accordance with some embodiments.

FIGS. 3 and 4 show exemplary interactive systems for facilitating user interaction according to some embodiments. As will be described in greater detail below, these interactive systems may include one or more electronic devices (e.g., a head-mounted-display device, a smart watch, a smart phone, etc.) that are worn by and/or interacted with by a user. In at least one embodiment, electronic devices of the interactive systems may include compliant electrodes that abut body portions of the user to conduct biopotential signals generated by the user's body. Such biopotential signals may be utilized by the interactive systems to detect physical facial movements (e.g., changes in gaze direction, facial gestures, facial expressions, etc.) made by the user based on characteristics (e.g., temporal characteristics, signal magnitude, signal phase shift, etc.) of the biopotential signals generated by the user's body.

FIG. 3 illustrates an exemplary interactive system 300 that may be galvanically coupled to a user 302 to facilitate interaction between user 302 and an electronic device or another user. As shown in this figure, system 300 may include a detection subsystem 304 for detecting facial movements made by user 302 based on characteristics of biopotential signals generated by the body of user 302. In some examples, detection subsystem 304 may include a gaze-detection subsystem 306 configured to identify a gaze direction of user 302 based on at least one characteristic of a biopotential signal generated by the eyes of user 302. Additionally or alternatively, detection subsystem 304 may include a gesture-detection subsystem 308 configured to identify a facial gesture of user 302 based on at least one characteristic of a biopotential signal generated by a facial muscle of user 302.

System 300 may also include a receiving subsystem 310 configured to sense biopotential signals generated by the body of user 302. Detection subsystem 304 and/or receiving subsystem 310 may be included in one or more electronic devices worn by and/or interacted with by user 302 and/or may be included in one or more external electronic devices. In some embodiments, system 300 may also include a display device 312 (e.g., a display of a head-mounted-display device) having a display region that is configured to display images to user 302. Display device 312 may include a display controller 314 that is configured to modify images displayed in the display region of display device 312 based on one or more facial movements of user 302 identified by detection subsystem 304. In at least one example, system 300 may also include a communication subsystem 316 configured to transmit data to an external device, such as a device not worn or interacted with by user 302. Communication subsystem 316 may, for example, be configured to modify data transmitted to the external device based on one or more identified facial movements of user 302 identified by detection subsystem 304.

In some embodiments, system 300 may include a facial coupling subsystem 318 that is galvanically coupled to user 302. For example, facial coupling subsystem 318 may be galvanically coupled to the body of user 302 via two or more compliant contact electrodes, such as compliant contact electrodes 320 and 322. Facial coupling subsystem 318 may include at least a portion of a single electronic device, such as a head-mounted-display device, or may include portions of two or more separate electronic devices. In some examples, compliant contact electrodes 320 and 322 may be disposed abutting a portion of the body of user 302 such that compliant contact electrodes 320 and 322 are in relatively close proximity to each other without directly contacting each other. In at least one example, compliant contact electrodes 320 and 322 may be separated from one another by a dielectric material and or be made of a conductive material (e.g., silver or silver chloride). In some examples, compliant contact electrodes 320 and 322 may conduct a biopotential signal generated by a biopotential source of user 302 (e.g., one of the biopotential sources described in connection with FIGS. 1 and 2). The biopotential signal may result in a differential signal being applied between compliant contact electrodes 320 and 322, which may be measured by receiving subsystem 310.

Characteristics of biopotential signals received by compliant contact electrodes 320 and 322 may be influenced by the dielectric properties of conductive tissues within the body of user 302. Additionally, as will be described in greater detail below, position, orientation, and/or movement of various portions of the body may influence signals. For example, a change in position, orientation, and/or movement of one or more portions of the body of user 302 may cause biopotential signal transmission pathways through the body to be lengthened, shortened, and/or otherwise changed.

FIG. 4 illustrates an exemplary interactive system 400 that may be capacitively coupled to a user 402 to facilitate interaction between user 402 and at least one electronic device and/or interactions between user 402 and other users. As shown in FIG. 4, system 400 may include a detection subsystem 404 for detecting facial movements made by user 402 based on characteristics of biopotential signals generated by the body of user 402. In some examples, detection subsystem 404 may include a gaze-detection subsystem 406 configured to identify a gaze direction of user 402 based on at least one characteristic of a biopotential signal generated by the eyes of user 402. Additionally or alternatively, detection subsystem 404 may include a gesture-detection subsystem 408 configured to identify a facial gesture of user 402 based on at least one characteristic of a biopotential signal generated by the body of user 402. System 400 may also include a receiving subsystem 410 for sensing biopotential signals that have been generated by the body of user 402. Detection subsystem 404 and/or receiving subsystem 410 may be included in one or more electronic devices worn by and/or interacted with by user 402 and/or may be included in one or more external electronic devices.

In some embodiments, system 400 may include a facial coupling subsystem 418 that is capacitively coupled to user 402. For example, facial coupling subsystem 418 may be capacitively coupled to the body of user 402 via two or more compliant non-contact electrodes, such as compliant non-contact electrodes 420 and 422, and one or more ground or reference electrodes, such as compliant contact electrode 424. As shown in FIG. 4, compliant non-contact electrodes, such as compliant non-contact electrodes 420 and 422, may abut a portion of the body of user 402 without physically contacting the body of user 402. Compliant non-contact electrodes 420 and 422 and compliant contact electrode 424 may be in relatively close proximity to each other and may be separated from one another by a dielectric material. Biopotential signals generated by the body of user 402 may induce an electric field within or around the body of user 402 that may cause a positive or negative charge to collect at one or more of compliant non-contact electrodes 420 and 422. Receiving subsystem 410 may measure the biopotential signals by measuring electric potentials between compliant non-contact electrodes 420 and 422 and/or compliant contact electrode 424.

According to at least one embodiment, biopotential signals received by receiving subsystem 410 via compliant electrodes 420-424 may be influenced by the dielectric properties of conductive tissues within the body of user 402. Additionally, as will be described in greater detail below, position, orientation, and/or movement of various portions of the body may influence the signal. For example, a change in position, orientation, and/or movement of one or more portions of the body of user 402 may cause biopotential signal transmission pathways through the body to be lengthened, shortened, and/or otherwise changed.

Figure 5:
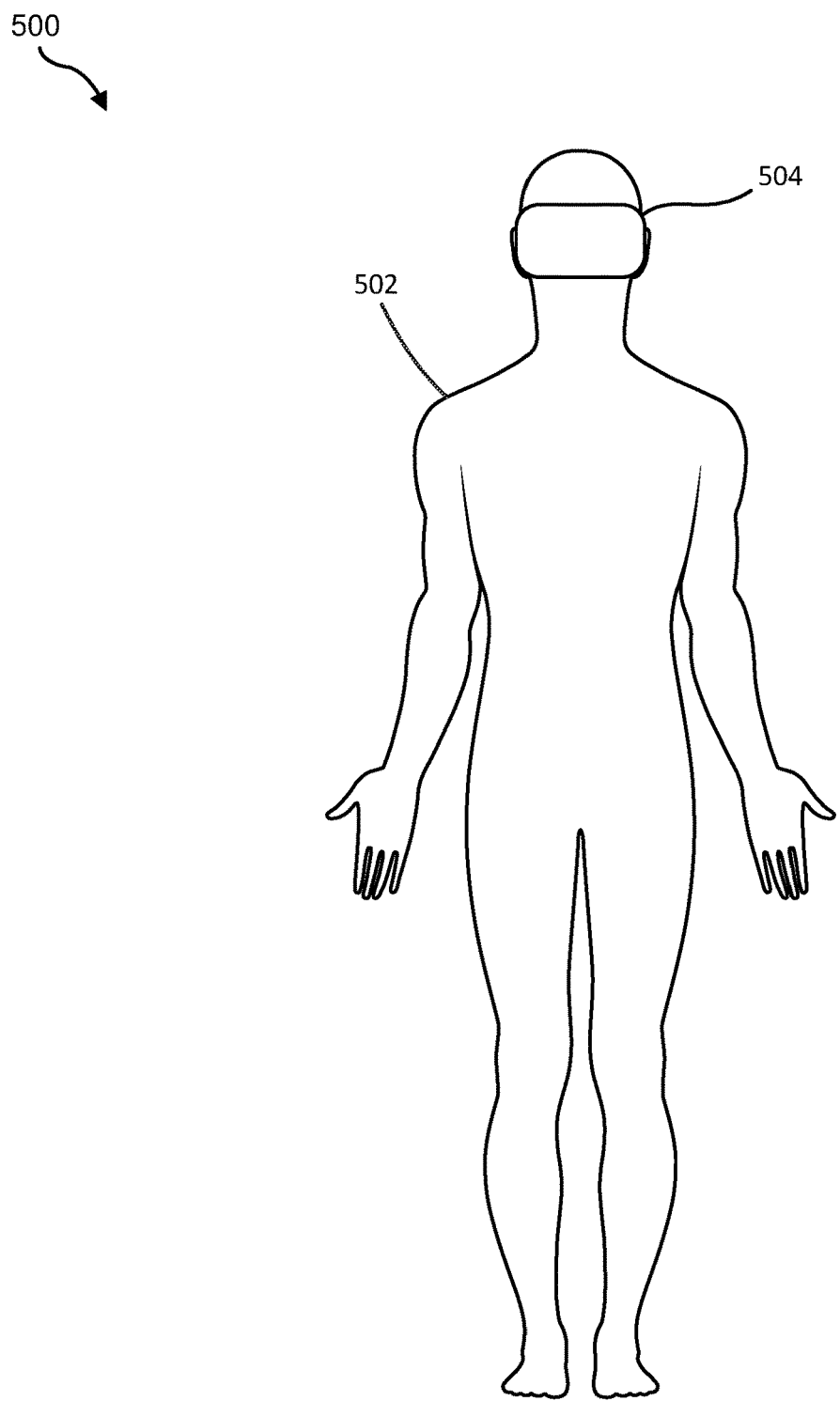
FIG. 5 is a front view of a user wearing a head-mounted-display device of an exemplary interactive system in accordance with some embodiments.
Figure 6:
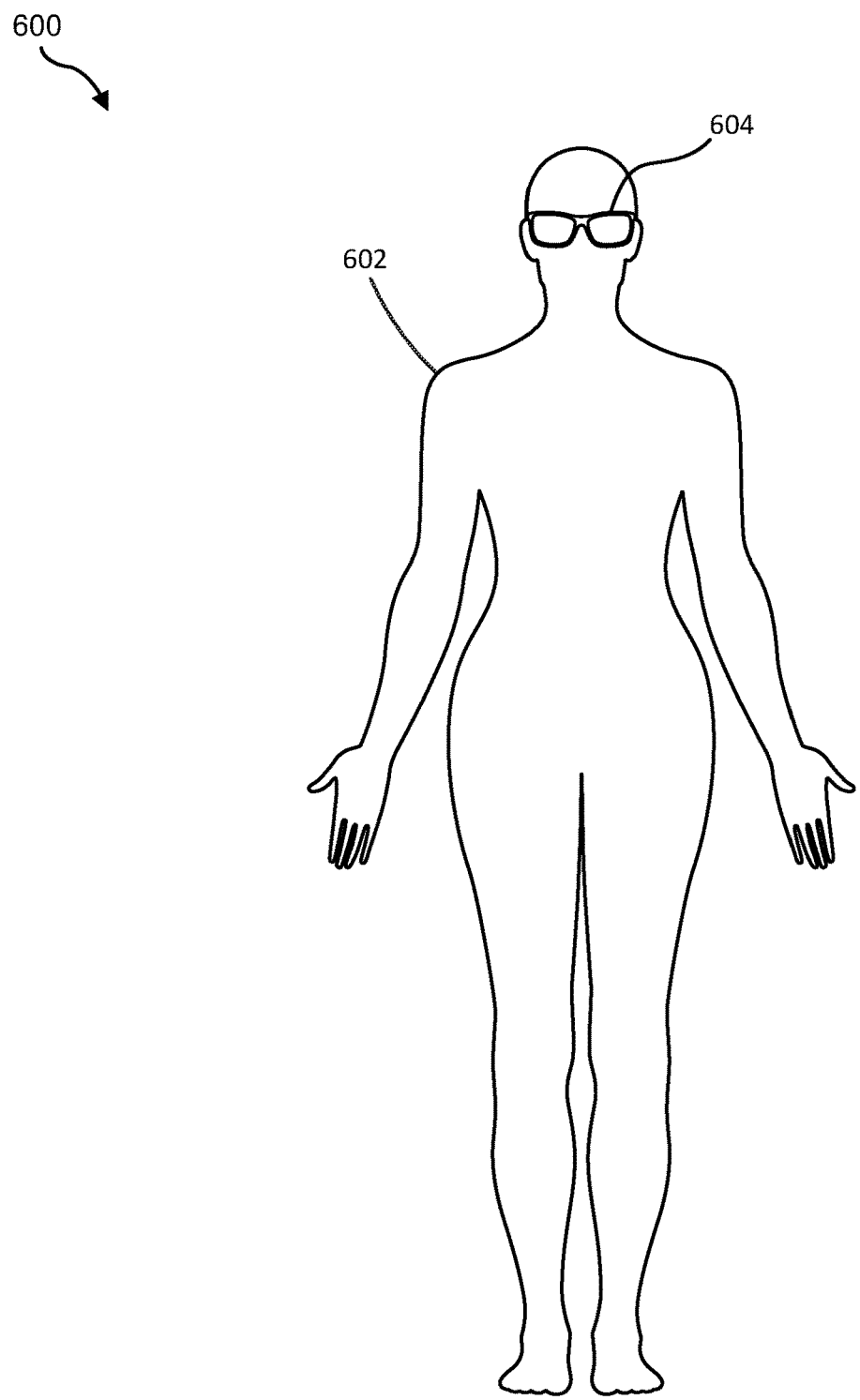
FIG. 6 is a front view of another user wearing a head-mounted-display device of another exemplary interactive system in accordance with some embodiments.

Example systems 300 and 400 in FIGS. 3 and 4 may be implemented in a variety of ways. For example, all or a portion of example systems 300 and 400 may represent portions of example systems 500 and 600 shown in FIGS. 5 and 6. As shown in FIG. 5, system 500 may include a user 502 and an electronic device worn by user 502. For example, FIG. 5 illustrates a head-mounted-display device 504, such as a virtual reality headset, worn on the head of user 502. As shown in FIG. 6, system 600 may include a user 602 and an electronic device worn by user 602. For example, FIG. 6 illustrates a head-mounted-display device 604, such as a pair of augmented reality glasses, worn on the head of user 602.

Figure 7:
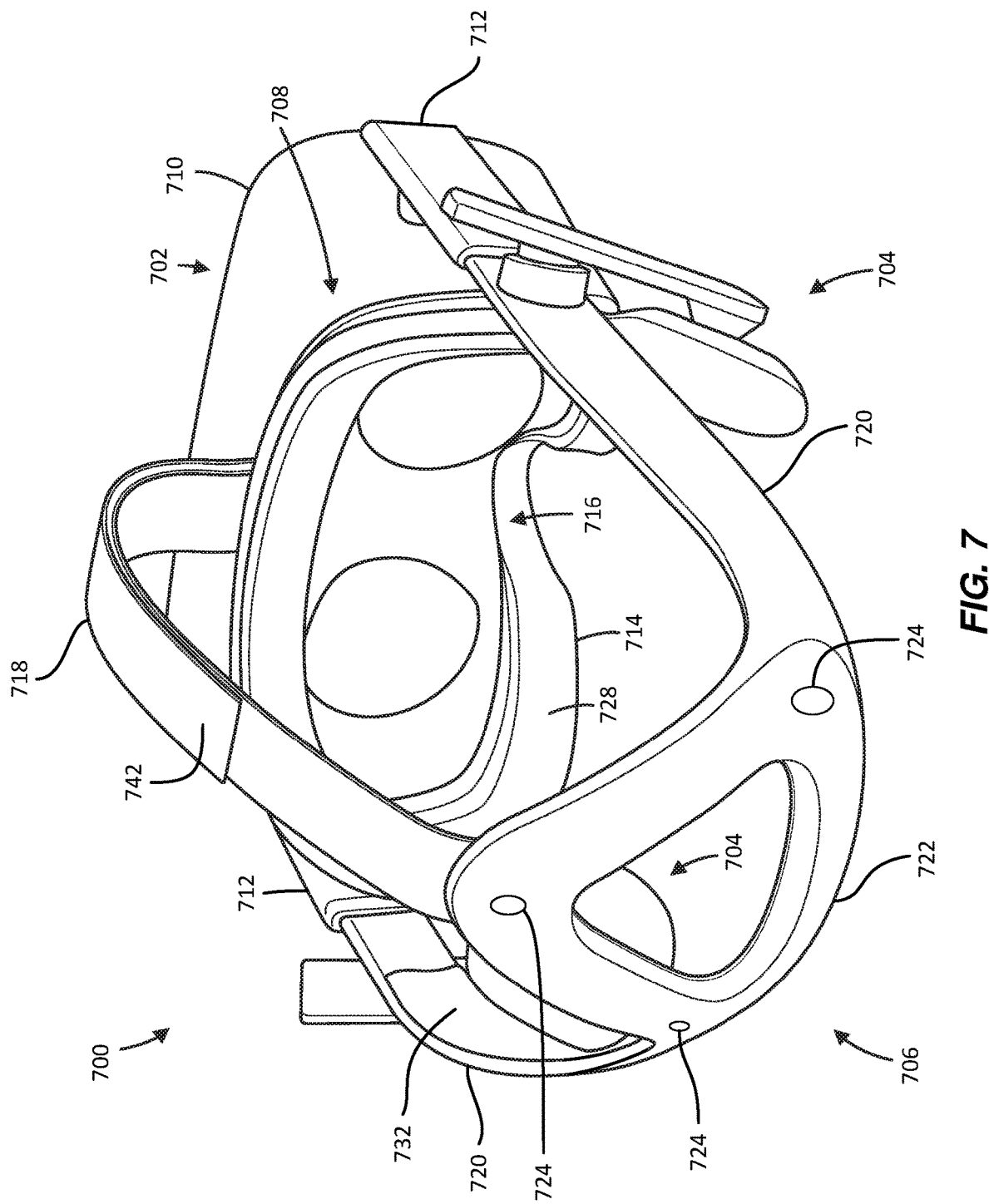
FIG. 7 is a perspective top view of an exemplary head-mounted-display device in accordance with some embodiments.
Figure 8:
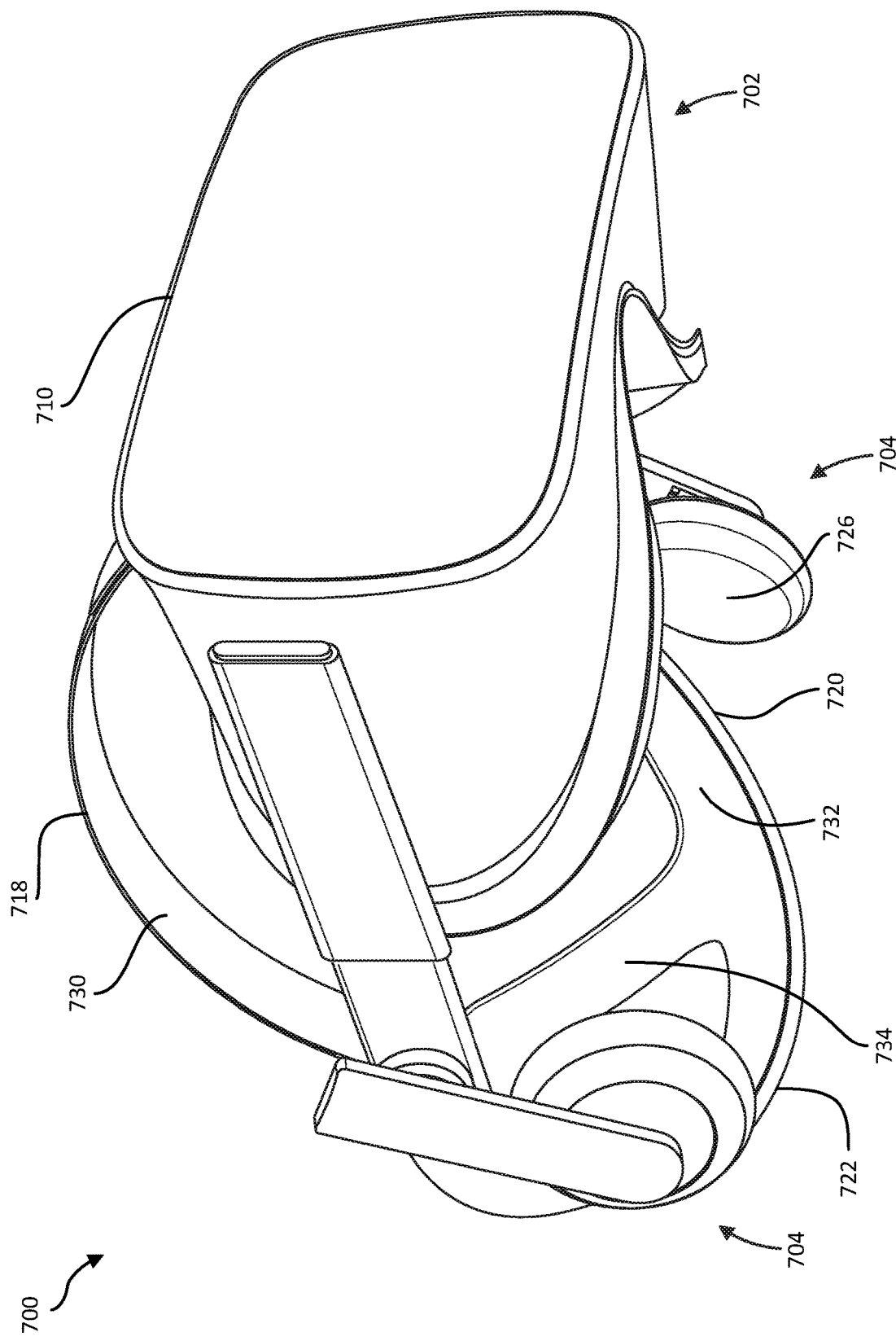
FIG. 8 is a perspective bottom view of the exemplary head-mounted-display device illustrated in FIG. 7 in accordance with some embodiments.

FIGS. 7 and 8 are perspective views of a head-mounted-display device 700 in accordance with some embodiments. As shown, head-mounted-display device 700 includes a head-mounted display 702, audio subsystems 704, a strap assembly 706, and a facial-interface subsystem 708. In some embodiments, the term "head-mounted display" may refer to any type or form of display device or system that is worn on or about a user's head and displays visual content to a user. Head-mounted displays may display content in any suitable manner, including via a screen (e.g., an LCD or LED screen), a projector, a cathode ray tube, an optical mixer, etc. Head-mounted displays may display content in one or more of various media formats. For example, a head-mounted display may display video, photos, and/or computer-generated imagery (CGI).

Head-mounted displays may provide diverse and distinctive user experiences. Some head-mounted displays may provide virtual-reality experiences (i.e., they may display computer-generated or pre-recorded content), while other head-mounted displays may provide real-world experiences (i.e., they may display live imagery from the physical world). Head-mounted displays may also provide any mixture of live and virtual content. For example, virtual content may be projected onto the physical world (e.g., via optical or video see-through), which may result in augmented reality or mixed reality experiences.

In some embodiments, head-mounted display 702 may include an outer housing 710 that may surround, contain, and protect various display, optical, and other electronic components of head-mounted display 702. Examples of electronic components may include, without limitation, sensors, output devices (e.g., lights, display devices, audio devices, haptic devices, etc.), wireless communication devices (e.g., antennae), and electrical signal or power transfer mediums (e.g., wires or cables). Examples of sensors that may be included in head-mounted display 702 may include, without limitation, gyroscopic sensors, accelerometers, altimeters, global positioning system devices, light sensors, audio sensors, power sensors, and/or any other sensor. Outer housing 710 may be attached to strap assembly 706 by interfaces 712. Facial-interface subsystem 708 may be configured to comfortably rest against a region of a user's face, including a region surrounding the user's eyes, when head-mounted-display device 700 is worn by the user. In these embodiments, facial-interface subsystem 708 may include a facial-interface cushion 714. Facial-interface cushion 714 may surround a viewing region 716 that includes the user's field of vision while the user is wearing head-mounted-display device 700.

In some embodiments, strap assembly 706 may be used to mount head-mounted display 702 on a user's head. As shown in FIG. 7, strap assembly 706 may include an upper strap 718 and lower straps 720. Lower straps 720 may each be coupled to one of strap interfaces 712, which are shown coupled to head-mounted display 702. Strap assembly 706 may adjustably conform to the top and/or sides of a user's head when the user is wearing head-mounted display 702. In some embodiments, strap assembly 706 may include a back piece 722 coupled with upper strap 718 and lower straps 720 to rest against the back of the user's head.

In some embodiments, strap assembly 706 may include various electronic components. As shown in FIG. 7, strap assembly 706 may include motion-tracking lights 724 integrated into back piece 722 and audio subsystems 704 coupled to lower straps 720. In some embodiments, motion-tracking lights 724 may be light-emitting-diode markers that are used by an external motion-tracking system to track the position and/or motion of head-mounted-display device 700.

Compliant electrodes made of various conductive elements for receiving biopotential signals generated by a user's body, such as compliant electrodes 320 and 322 in FIG. 3 or compliant electrodes 420, 422, or 424 in FIG. 4, may be incorporated into head-mounted-display device 700. In some embodiments, these conductive elements may receive biopotential signals generated by a user's body. Conductive elements may be incorporated into any suitable surface of head-mounted-display device 700. In some examples, the medial surfaces of head-mounted-display device 700 may include one or more conductive elements positioned to rest against or near a user's head, face, or ears. For example, conductive elements may be incorporated into some or all of medial surfaces 726 of audio subsystems 704, a medial surface 728 of facial-interface subsystem 708, a medial surface 730 of upper strap 718, medial surfaces 732 of lower straps 720, and/or a medial surface 734 of back piece 722.

Figure 9A:
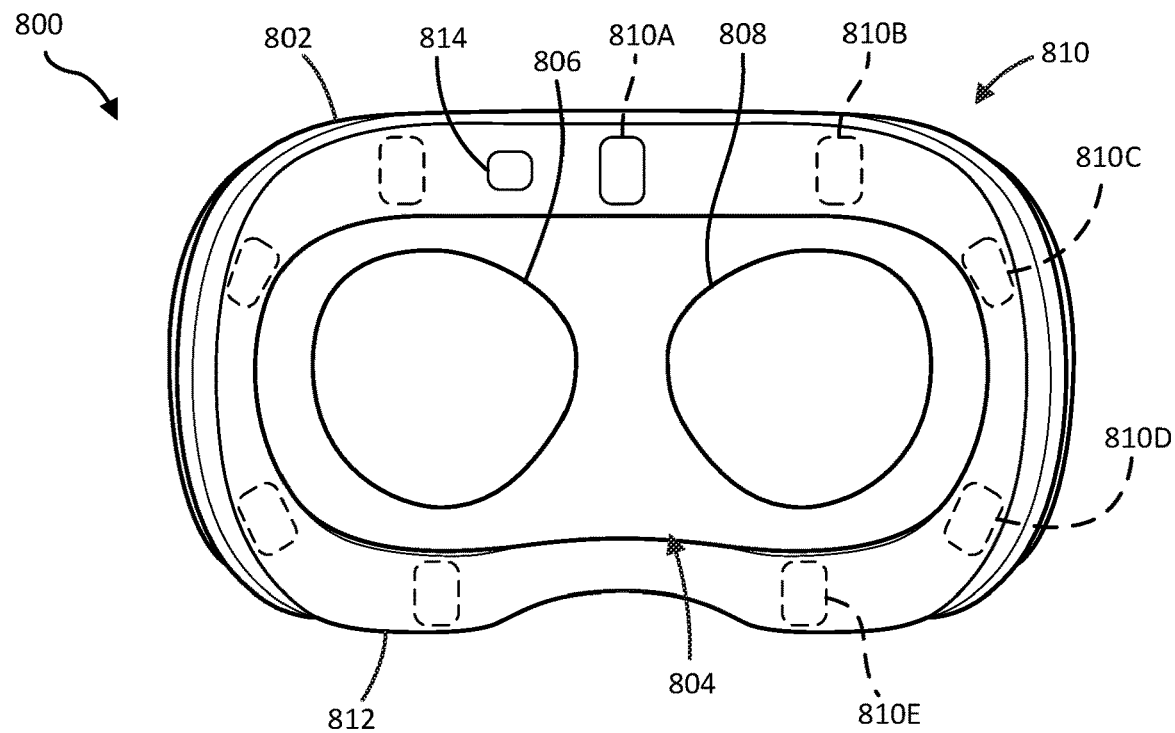
FIGS. 9A and 9B are perspective views of exemplary electrodes of the head-mounted-display device illustrated in FIG. 7 in accordance with some embodiments.
Figure 9B:
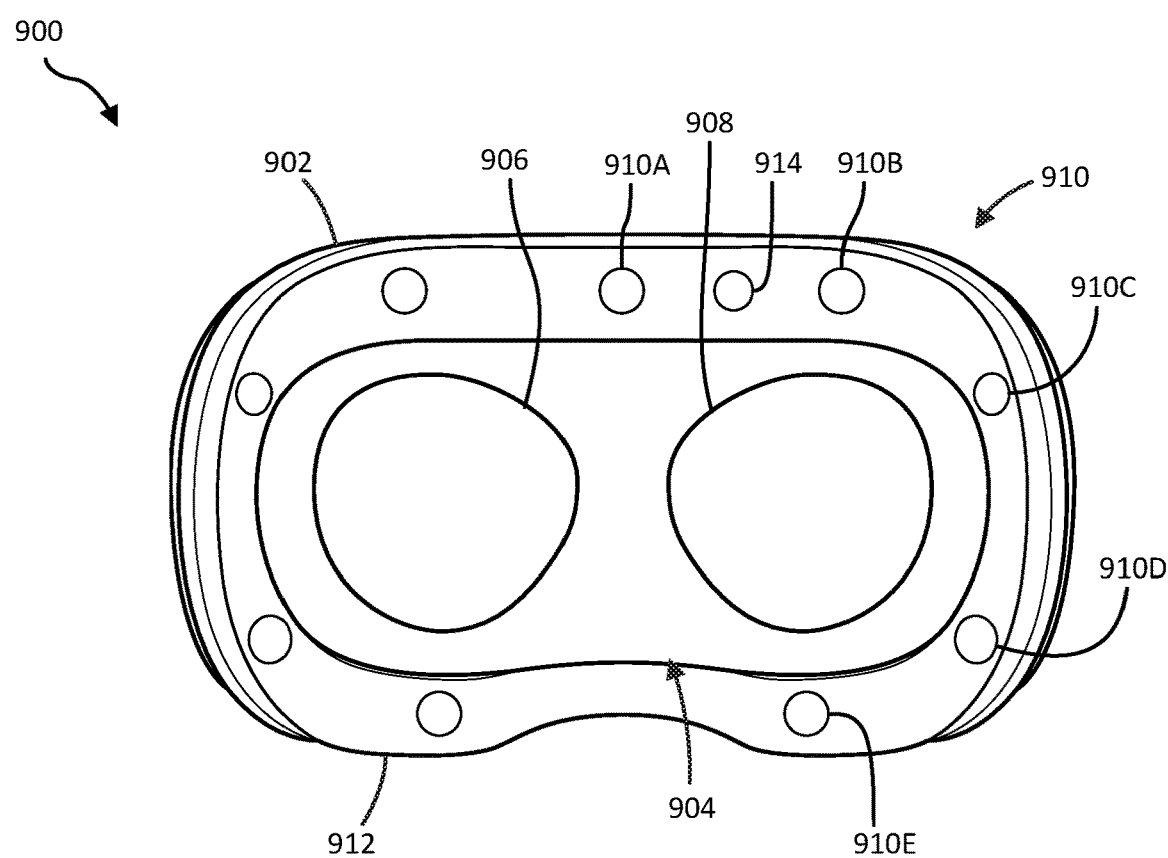

FIGS. 9A and 9B are front views of exemplary head-mounted-display devices in accordance with some embodiments. Head-mounted-display devices, such as head-mounted-display device 700 shown in FIGS. 7 and 8, may include facial interfaces having compliant electrodes of a facial coupling subsystem as described herein. Such facial interfaces may include any suitable number of compliant electrodes having any suitable size, shape, and configuration.

According to at least one embodiment, as shown in FIG. 9A, a head-mounted-display device 800 may include a facial interface 802 surrounding a viewing region 804, which includes a user's field of vision, allowing the user to look through left-eye lens 806 and right-eye lens 808 of head-mounted-display device 800 without interference from outside light while the user is wearing head-mounted-display device 800. Images displayed by one or more display screens of head-mounted-display device 800 may be visible to a user through left-eye lens 806 and right-eye lens 808.

As illustrated in FIG. 9A, facial interface 802 may also include a plurality of compliant electrodes 810 that are positioned to abut various regions of a user's face when head-mounted-display device 800 is worn by the user. For example, as will be described in greater detail below, compliant electrodes 810 may be positioned to abut portions of the user's nasal, cheek, temple, and/or forehead facial regions. In at least one embodiment, one or more of compliant electrodes 810 may be elongated compliant electrodes having a rectangular or generally rectangular periphery, as shown in FIG. 9A. In some examples, compliant electrodes 810 may be disposed in a facial-interface cushion 812 of facial interface 802 such that surfaces of compliant electrodes 810 positioned to abut the user's face are aligned or generally aligned with adjacent surface regions of facial-interface cushion 812 positioned to abut the user's face. Compliant electrodes 810 may be positioned apart from each other such that adjacent compliant electrodes 810 do not contact each other. In some examples, facial-interface cushion 812 may include an insulative material that prevents an electrical current from being conducted between separate compliant electrodes 810 via facial-interface cushion 812.

Compliant electrodes 810 may be galvanically or capacitively coupled to a user when head-mounted-display device 800 is worn by the user such that biopotential signals generated by a user's body may be conducted by compliant electrodes 810. Compliant electrodes 810 may be configured to receive biopotential signals when compliant electrodes 810 contact a user's skin and/or when compliant electrodes 810 are disposed and within sufficiently close proximity to the user's skin.

According to at least one embodiment, compliant electrodes 810 may include at least one compliant electrode (e.g., compliant electrode 810A), which is electrically connected to a receiving subsystem, configured as a ground or reference electrode. As shown in FIG. 9A, compliant electrode 810A may be a compliant contact electrode that is positioned to physically contact a user's skin. Compliant electrodes 810 may also include one or more receiving electrodes (e.g., compliant electrodes 810B-810E), which are electrically connected to the receiving subsystem, that are each configured to receive a biopotential signal generated by the user's body. As shown in FIG. 9A, compliant electrodes 810B-810E may be compliant non-contact electrodes that are integrated into or hidden within facial-interface cushion 812 such that they do not physically contact a user's skin. In some examples, a biopotential signal generated by the user's body may be received by each of the receiving electrodes at a different point in time or with various other different characteristics.

According to some embodiments, head-mounted-display device 800 may be configured to receive biopotential signals for detecting facial movements (e.g., changes in gaze direction, facial expressions, facial positions, facial movements, etc.). In some embodiments, a plurality of biopotential signals having different characteristics (e.g., different frequencies) may be received via one or more of compliant electrodes 810 of head-mounted-display device 800. For example, a plurality of EOG and/or EMG biopotential signals having different characteristics may be consecutively generated by a user's body and/or may be consecutively received from the user's body via one or more of compliant electrodes 810.

In some examples, characteristics of the biopotential signals conducted from a user's body may be affected by temperature, moisture, sweat, or other factors. As such, in some examples, head-mounted-display device 800 may also include a sensor 814 (e.g., a temperature sensor, a humidity sensor, a moisture sensor, a sweat sensor, etc.) configured to measure temperature, moisture, sweat, or other factors that affect characteristics of biopotential signals such that the systems described herein may account for the effects of these factors when using biopotential signals to track facial movements.

According to at least one embodiment, as shown in FIG. 9B, a head-mounted-display device 900 may include a facial interface 902 surrounding a viewing region 904, which includes a user's field of vision, allowing the user to look through left-eye lens 906 and right-eye lens 908 of head-mounted-display device 900 without interference from outside light while the user is wearing head-mounted-display device 900. Images displayed by one or more display screens of head-mounted-display device 900 may be visible to a user through left-eye lens 906 and right-eye lens 908.

As illustrated in FIG. 9B, facial interface 902 may also include a plurality of compliant electrodes 910 that are positioned to abut various regions of a user's face when head-mounted-display device 900 is worn by the user. For example, as will be described in greater detail below, compliant electrodes 910 may be positioned to abut portions of the user's nasal, cheek, temple, and/or forehead facial regions. In at least one embodiment, one or more of compliant electrodes 910 may be compliant electrodes having a circular or generally circular periphery, as shown in FIG. 9B. In some examples, compliant electrodes 910 may be disposed in a facial-interface cushion 912 of facial interface 902 such that surfaces of compliant electrodes 910 positioned to abut the user's face are aligned or generally aligned with adjacent surface regions of facial-interface cushion 912 positioned to abut the user's face. Compliant electrodes 910 may be positioned apart from each other such that adjacent compliant electrodes 910 do not contact each other. In some examples, facial-interface cushion 912 may include an insulative material that prevents an electrical current from being conducted between separate compliant electrodes 910 via facial-interface cushion 912.

Compliant electrodes 910 may be galvanically coupled to a user when head-mounted-display device 900 is worn by the user such that biopotential signals generated by a user's body may be conducted by compliant electrodes 910. Compliant electrodes 910 may be configured to receive biopotential signals when compliant electrodes 910 contact a user's skin.

According to at least one embodiment, compliant electrodes 910 may include at least one compliant electrode (e.g., compliant electrode 910A), which is electrically connected to a receiving subsystem, configured as a ground or reference electrode. As shown in FIG. 9B, compliant electrode 910A may be a compliant contact electrode that is positioned to physically contact a user's skin. Compliant electrodes 910 may also include one or more receiving electrodes (e.g., compliant electrodes 910B-910E), which are electrically connected to the receiving subsystem, that are each configured to receive a biopotential signal generated by the user's body. As shown in FIG. 9B, compliant electrodes 910B-910E may be compliant contact electrodes that are integrated into facial-interface cushion 912 such that they physically contact a user's skin. In some examples, a biopotential signal generated by the user's body may be received by each of the receiving compliant electrodes at a different point in time or with different characteristics.

According to some embodiments, head-mounted-display device 900 may be configured to receive biopotential signals for detecting facial movements (e.g., changes in gaze direction, facial expressions, facial positions, facial movements, etc.). In some embodiments, a plurality of biopotential signals having different characteristics (e.g., different frequencies) may be received via one or more of compliant electrodes 910 of head-mounted-display device 900. For example, a plurality of EOG and/or EMG biopotential signals having different characteristics may be consecutively generated by a user's body and/or may be consecutively received from the user's body via one or more of compliant electrodes 910.

In some examples, characteristics of biopotential signals conducted from a user's body may be affected by temperature, moisture, sweat, or other factors. As such, in some examples, head-mounted-display device 900 may also include a sensor 914 (e.g., a temperature sensor, a humidity sensor, a moisture sensor, a sweat sensor, etc.) configured to measure temperature, moisture, sweat, or other factors that affect characteristics of biopotential signals such that the systems described herein may account for the effects of these factors when using biopotential signals to detect facial movements.

Figure 10:
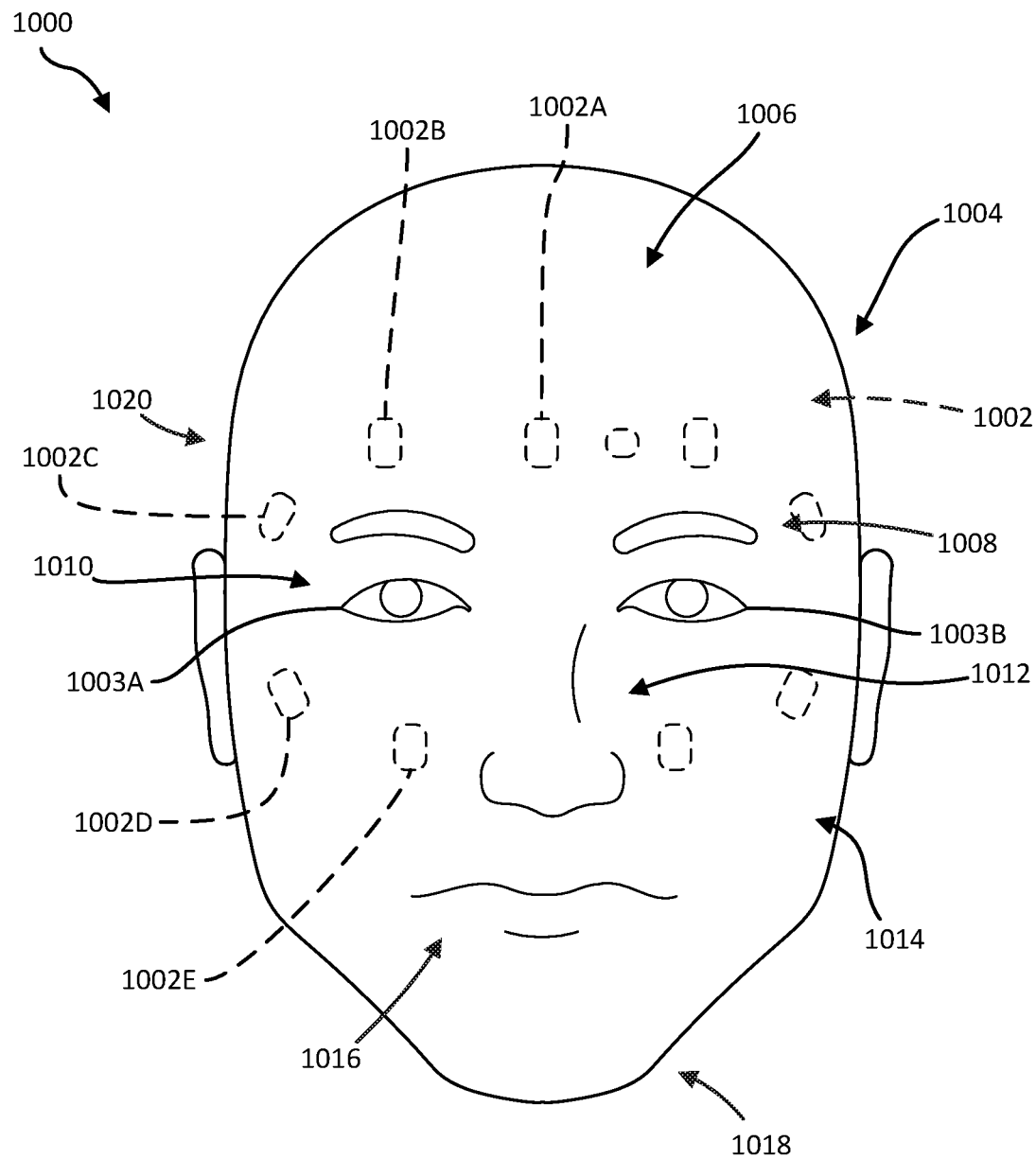
FIG. 10 is a view of a head of a user showing exemplary locations of electrodes of a head-mounted-display device worn by the user in accordance with some embodiments.

FIG. 10 shows a head 1000 of a user interacting with an exemplary head-mounted-display device, such as head-mounted-display device 800 shown in FIG. 9A. As shown in FIG. 10, a head-mounted-display device may be positioned on head 1000 of the user such that compliant electrodes (e.g., compliant electrodes 810 shown in FIG. 9A) of the head-mounted-display device abut various regions 1002 of the user's face 1004. For reference, FIG. 10 illustrates exemplary regions 1002A-E corresponding to compliant electrodes 810A-E of head-mounted-display device 800, respectively. As shown in this example, compliant electrodes 810B and 810C may be positioned above the user's right eye 1003A when head-mounted-display device 800 is worn by the user, and compliant electrodes 810D and 810E may be positioned below the user's right eye 1003A when head-mounted-display device 800 is worn by the user. In some examples, as shown in FIG. 10, compliant electrodes 810A-E may be positioned such that none of compliant electrodes 810A-E are vertically or horizontally aligned when head-mounted-display device 800 is worn by the user and the user's eyes 1003 are level.

Compliant electrodes 810 of head-mounted-display device 800 may be utilized, as part of an interactive system (e.g., systems 300 and 400 shown in FIGS. 3 and 4, respectively) to detect facial movements in any suitable regions of head 1000 of the user, including gaze directions of eyes 1003 of the user and/or facial gestures in various portions of face 1004 of the user. For example, compliant electrodes 810 may be utilized by a detection system (e.g., detection subsystem 304 or 404 shown in FIGS. 3 and 4) to detect facial movements in and/or near one or more regions of head 1000 of the user, including forehead region 1006, brow region 1008, eye region 1010, nasal region 1012, cheek region 1014, mouth region 1016, chin region 1018, temple region 1020, and/or any other suitable region.

In some embodiments, biopotential signals may be received at various regions 1002 of the user's face 1004 via one or more compliant electrodes 810 of head-mounted-display device 800. For example, biopotential signals may be generated by one or more of the biopotential-signal sources described in FIGS. 1 and 2. The biopotential signals may pass through head 1000 of the user, including at least a portion of face 1004, and/or through other portions of a user's body and may be received by head-mounted-display device 800 at one or more contact regions 1002 of face 1004 of the user via one or more of compliant electrodes 810. As the biopotential signals pass from the user's head 1000 and/or through other portions of the user's body, the biopotential signals may be delayed or attenuated due to various dielectric properties of the user's head 1000 and/or body such that the propagation delays of received signals are different at different contact regions 1002, the magnitudes of the received signals are decreased in comparison to the generated signals, and/or such that the phases of the received signals are shifted in comparison to the generated signals.

In some examples, an amount of propagation delay or attenuation may be affected by positions of various biopotential-signal sources relative to compliant electrodes 810. Accordingly, biopotential signals may be evaluated and correlated to various eye movements and facial gestures (e.g., facial expressions, combinations of facial expressions, and/or other facial positions) of the user. For example, facial positions corresponding to various facial gestures may correlate to relatively longer or shorter path lengths for biopotential signals generated by the user's body, resulting in greater or lesser amounts of propagation delay or attenuation of the biopotential signals. For example, a biopotential signal generated by a user's frontalis muscle 212 subsequently received by one or more of compliant electrodes 810 may be stronger at compliant electrodes closer to the user's frontalis muscle 212 (e.g., compliant electrode 810B) and weaker at compliant electrodes further away from the user's frontalis muscle 212 (e.g., compliant electrode 810E).

Characteristics of biopotential signals may be correlated to user facial movements, such as facial gestures and/or other facial gestures, in any suitable manner. For example, observations of biopotential signals may be correlated to user facial movements using, for example, machine learning (e.g., supervised or unsupervised learning), computational statistics, and/or any other suitable analytical methodology. In some embodiments, a detection subsystem (e.g., detection subsystem 304 and/or 404 shown in FIGS. 3 and 4) may utilize a machine-learning model that uses measured biopotential signals having one or more characteristics that have been received by various compliant electrodes 810 and/or combinations of compliant electrodes 810. Amplitudes, phase-shifts, propagation delay, and/or any other suitable characteristics of such biopotential signals may be correlated through such a methodology to various user facial movements and/or combinations of gestures. Such a model may be specific to a particular user and/or may be more generally generated by multiple users. In some examples, the detection subsystem may be configured to identify various facial movements based on a comparison between at least one characteristic of one or more biopotential signals and at least one predetermined signal characteristic. For example, threshold signal magnitudes and/or phase shift amounts may be utilized to determine whether one or more biopotential signals are indicative of a user facial movement, such as a facial expression. In at least one example, at least one predetermined signal characteristic, such as a signal threshold value, may be based on at least one characteristic of one or more biopotential signals received during at least one of a time period during which a user is making a facial gesture and a time period during which the user is not making a facial gesture (e.g., during training of a machine-learning model or other model).

Compliant electrodes for conducting biopotential signals may have various configurations and may be integrated into the facial coupling subsystems described herein in a variety of ways. FIGS. 11-20 illustrate various exemplary compliant electrodes and compliant-electrode configurations for facial coupling subsystems of head-mounted-display devices (e.g., facial interface 802 of head-mounted-display device 800 in FIG. 9A) according to some embodiments.

Figure 11A:
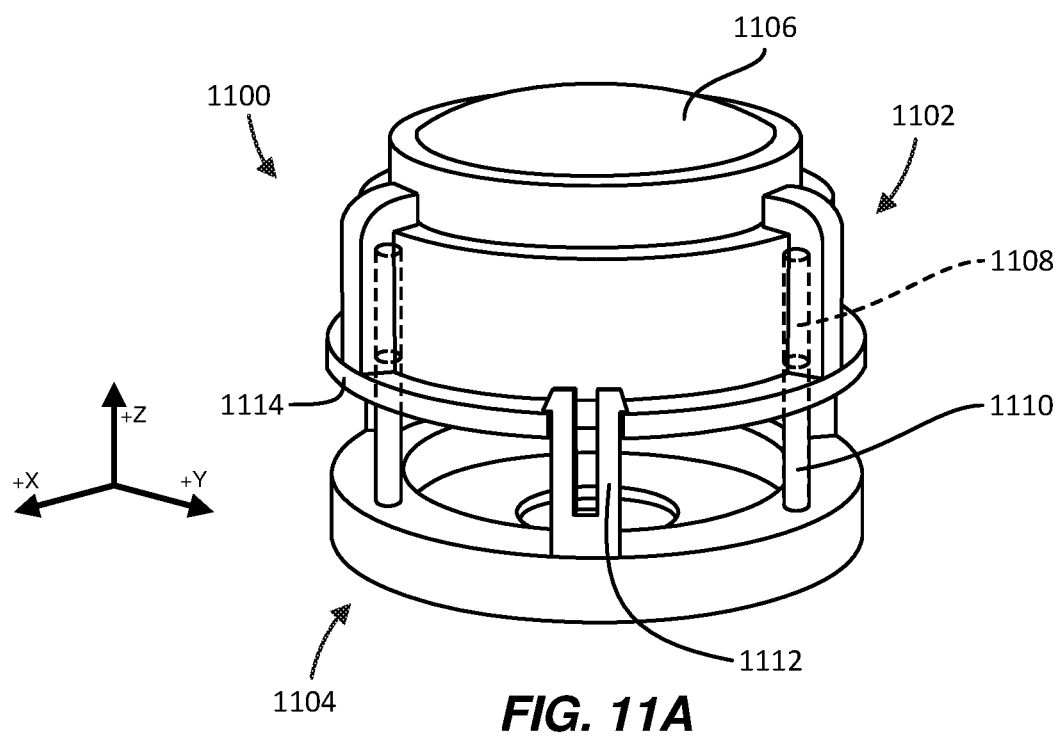
FIGS. 11A and 11B are perspective views of an exemplary compliant electrode in accordance with some embodiments.
Figure 11B:
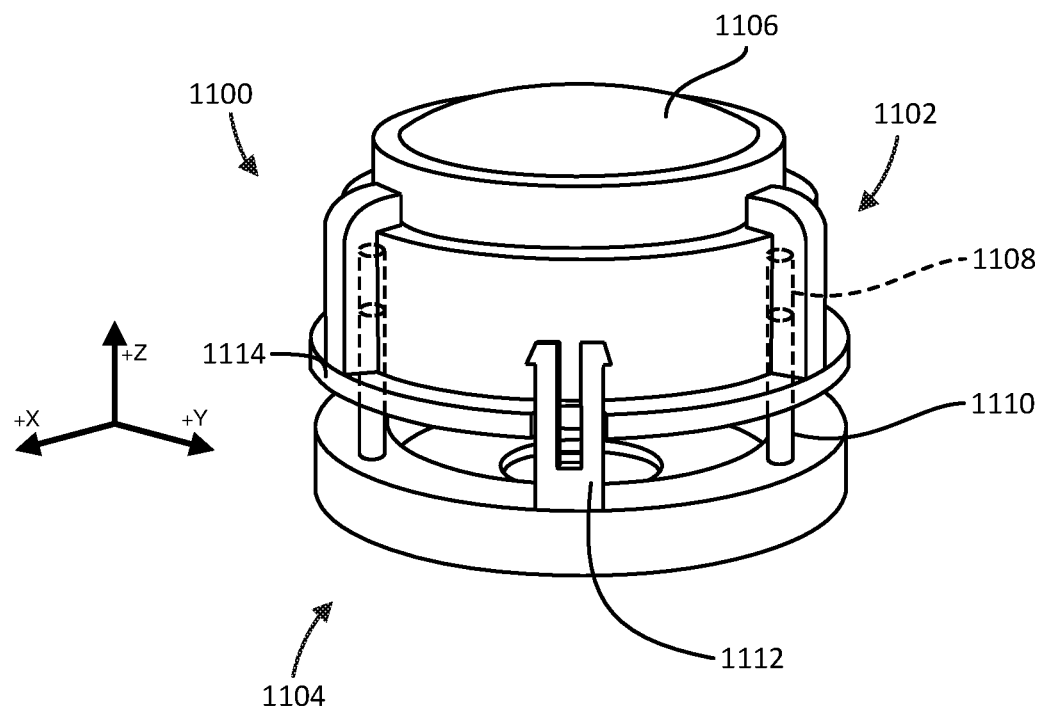

FIGS. 11A and 11B illustrate an exemplary compliant electrode 1100. As shown in these figures, compliant electrode 1100 may include a user-side component 1102 and a display-side component 1104. User-side component 1102 and display-side component 1104 may be constructed from any suitable material (e.g., plastic or aluminum). In some examples, display-side component 1104 may be coupled to or integrated with a frame or housing of a head-mounted-display device. As such, movement of display-side component 1104 may be restricted relative to the head-mounted display device. As shown in FIGS. 11A and 11B, user-side component 1102 may be configured to freely move in the illustrated Z direction (e.g., a direction normal to the surface of a user's face) but resist motion in the illustrated X and Y directions (e.g., directions tangent to the surface of the user's face).

User-side component 1102 may include a top surface 1106 that may include one or more conductive elements (not shown) for conducting biopotential signals generated by a user's body and one or more sockets 1108 that are mateable to legs or pins 1110 of display-side component 1104. In some examples, sockets 1108 and pins 1110 may enable, when engaged, user-side component 1102 of compliant electrode 1100 to freely move in the illustrated Z direction but resist motion in the illustrated X and Y directions. In some examples, display-side component 1104 may include a retention element 1112 that is configured to catch on a lip 1114 of user-side component 1102 in order to prevent pins 1110 from disengaging sockets 1108. In some examples, compliant electrode 1100 may include a compliant element (e.g., a compliant foam or a spring) between user-side component 1102 and display-side component 1104 that is configured to apply a force against user-side component 1102 and display-side component 1104.

Figure 12:
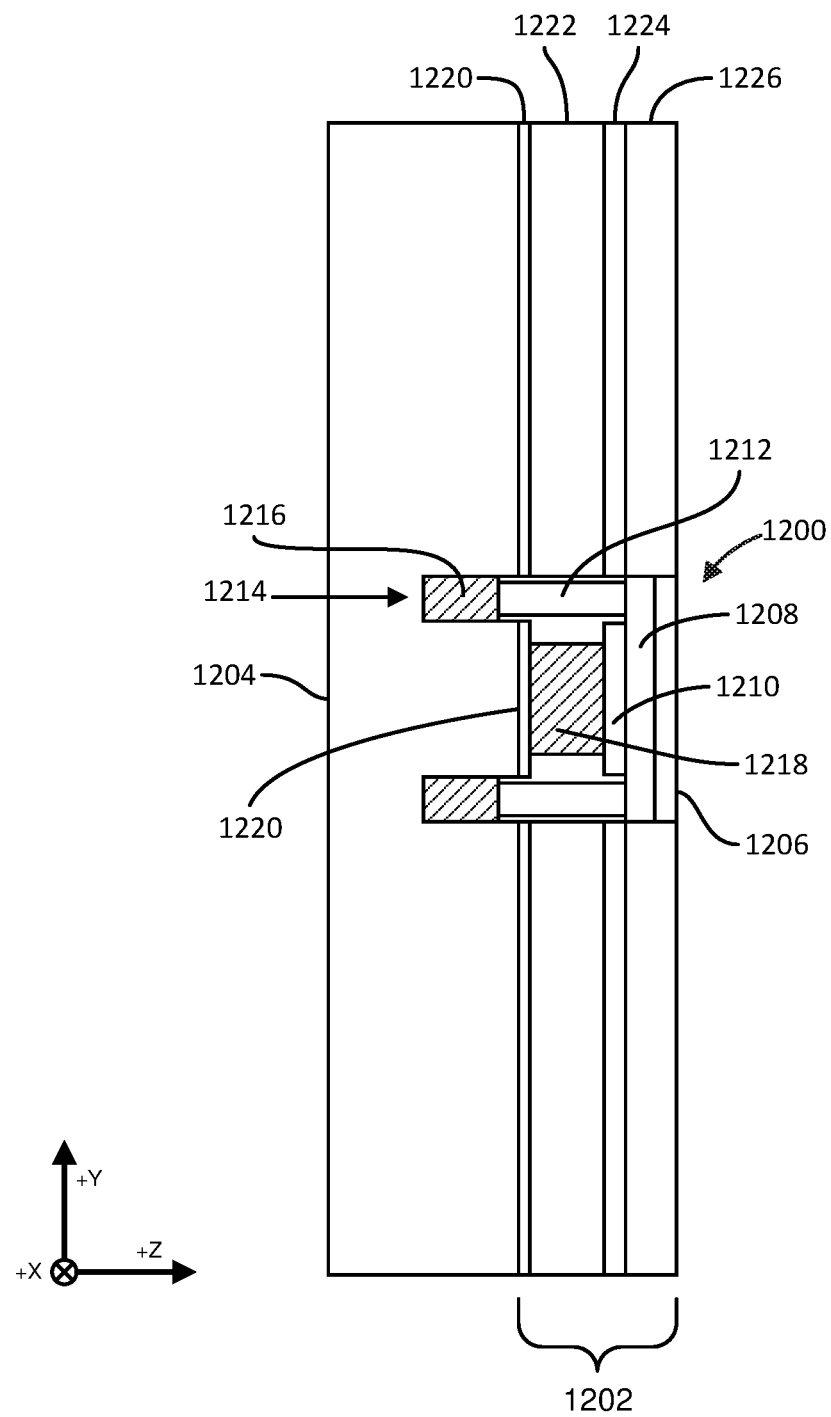
FIG. 12 is a cross-sectional view of an exemplary compliant electrode configuration in accordance with some embodiments.

FIG. 12 illustrates a compliant contact electrode 1200 integrated into a portion of a facial-interface subsystem 1202, which is attached to a frame 1204 of a head-mounted display. As shown in this example, compliant contact electrode 1200 may include a conductive surface 1206 configured to contact a user's skin and a rigid board 1208 (e.g., a printed circuit board) that electrically couples conductive surface 1206 to signal-receiving circuitry 1210 (e.g., analog conditioning circuits, amplifiers, capacitors, resistors, etc.). In this example, compliant contact electrode 1200 may include one or more legs or pins 1212 that are mateable to an opposing interface 1214 (e.g., a hole) of frame 1204. In some examples, the mating of legs 1212 to interface 1214 may substantially prevent compliant contact electrode 1200 from moving in any direction tangent to the surface of a user's face (e.g., the illustrated X direction or the illustrated Y direction). One or more compliant elements 1216 and 1218 may be configured to allow compliant contact electrode 1200 to move in a direction normal to a surface of the user's face (e.g., the illustrated Z direction) while applying a restoring force against compliant electrode 1200. As shown in FIG. 12, facial-interface subsystem 1202 may include a shielding layer 1220 (e.g., copper tape or a conductive coating), a compliant layer 1222, a flex-circuit layer 1224 (e.g., electrical connections and/or additional shielding), and a compliant layer 1226.

Compliant element 1216, compliant element 1218, compliant layer 1222, and compliant layer 1226 may be made of any suitable compliant material. For example, compliant element 1216, compliant element 1218, compliant layer 1222, and compliant layer 1226 may each be made of a compliant foam, rubber, or polymer with a suitable thickness and stiffness. In at least one example, compliant element 1216, compliant element 1218, and compliant layer 1222 may be made of a compliant foam whose stiffness is less than the stiffness of a compliant foam from which compliant layer 1226 is made.

Figure 13:
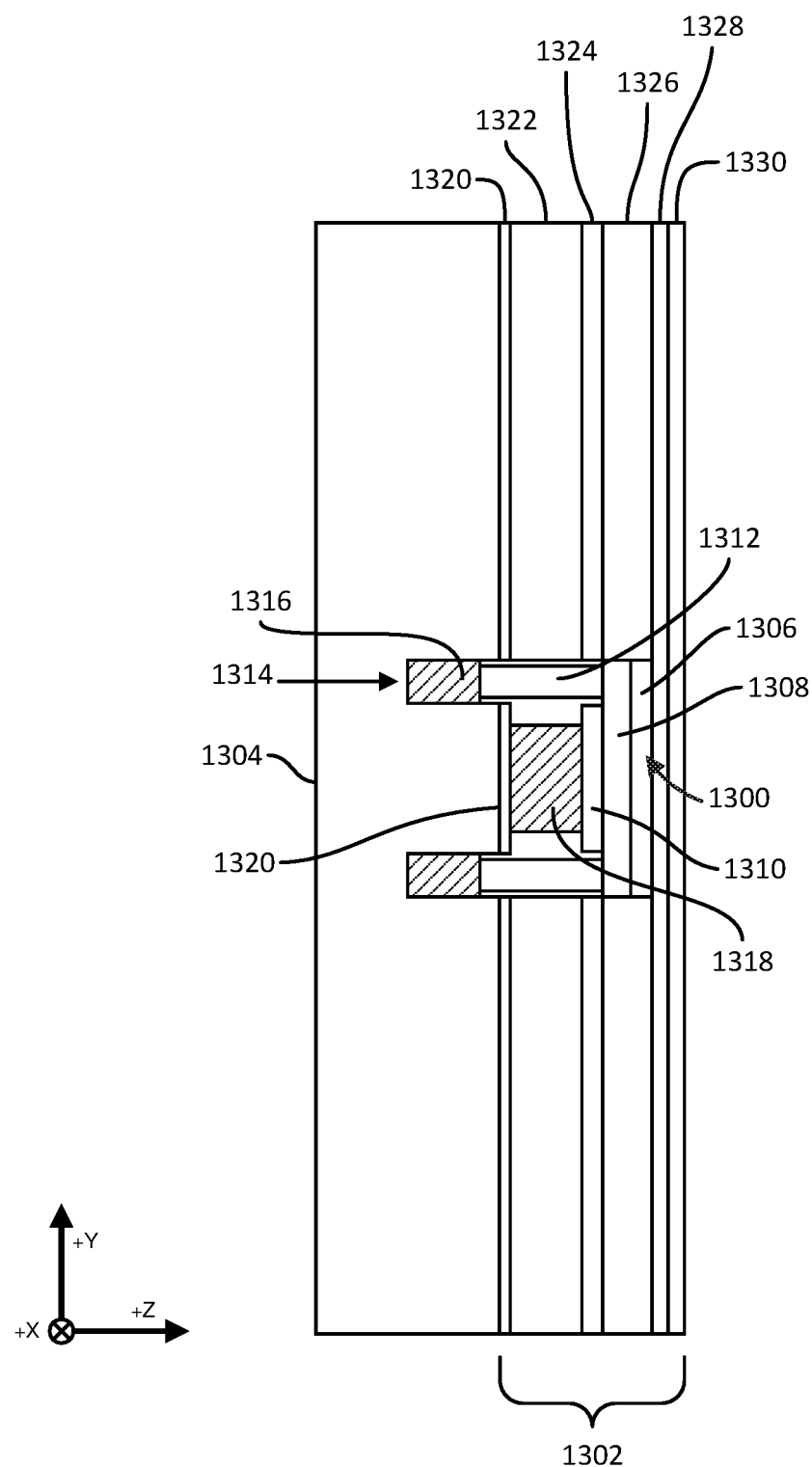
FIG. 13 is a cross-sectional view of an additional exemplary compliant electrode configuration in accordance with some embodiments.

FIG. 13 illustrates a compliant non-contact electrode 1300 integrated into a portion of a facial-interface subsystem 1302, which is attached to a frame 1304 of a head-mounted display. As shown in this example, compliant non-contact electrode 1300 may include a capacitive plate 1306 configured to conduct a biopotential signal and a rigid board 1308 (e.g., a printed circuit board) that electrically couples capacitive plate 1306 to signal-receiving circuitry 1310 (e.g., analog conditioning circuits, amplifiers, capacitors, resistors, etc.). In this example, compliant non-contact electrode 1300 may include one or more legs or pins 1312 that are mateable to an opposing interface 1314 of frame 1304. In some examples, the mating of legs 1312 to interface 1314 may substantially prevent compliant non-contact electrode 1300 from moving in any direction tangent to the surface of a user's face (e.g., the illustrated X direction or the illustrated Y direction). One or more compliant elements 1316 and 1318 may be configured to allow compliant non-contact electrode 1300 to move in a direction normal to a surface of the user's face (e.g., the illustrated Z direction) while applying a restoring force against electrode 1300.

As shown in FIG. 13, facial-interface subsystem 1302 may include a shielding layer 1320 (e.g., copper tape or a conductive coating), a compliant layer 1322, a flex-circuit layer 1324 (e.g., electrical connections and/or additional shielding), a compliant layer 1326, a compliant layer 1328, and a compliant layer 1330. Compliant elements 1316 and 1318 and compliant layers 1324-1330 may each be made of any suitable compliant material. For example, compliant elements 1316 and 1318 and compliant layers 1324-1330 may each be made of a compliant foam with a suitable thickness and stiffness. In some examples, compliant element 1316, compliant element 1318, and compliant layer 1322 may be made of a compliant foam whose stiffness is equal to $k_1$, compliant layer 1324 may be made of a compliant foam whose stiffness is equal to $k_2$, compliant layer 1328 may be made of a compliant foam whose stiffness is equal to $k_3$, and compliant layer 1330 may be made of a compliant foam whose stiffness is equal to $k_4$. In at least one example, $k_4 > k_3 > k_2 > k_1$. In some examples, compliant layers 1328 and 1330 may be made to be substantially incompressible such that a distance between capacitive plate 1306 and a surface of a user's face remains substantially constant.

Figure 14A:
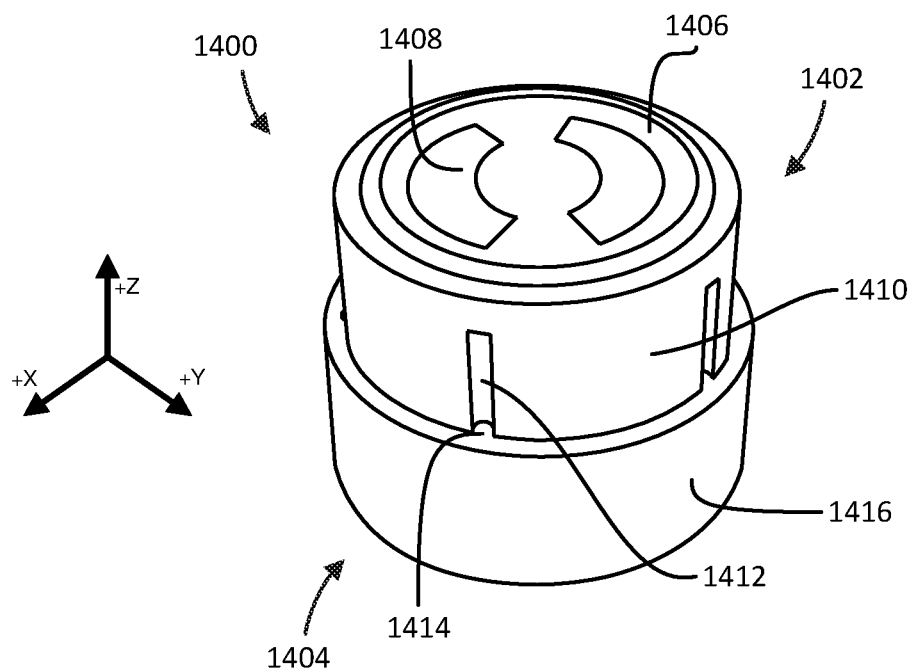
FIGS. 14A and 14B are perspective views of an additional exemplary compliant electrode in accordance with some embodiments.
Figure 14B:
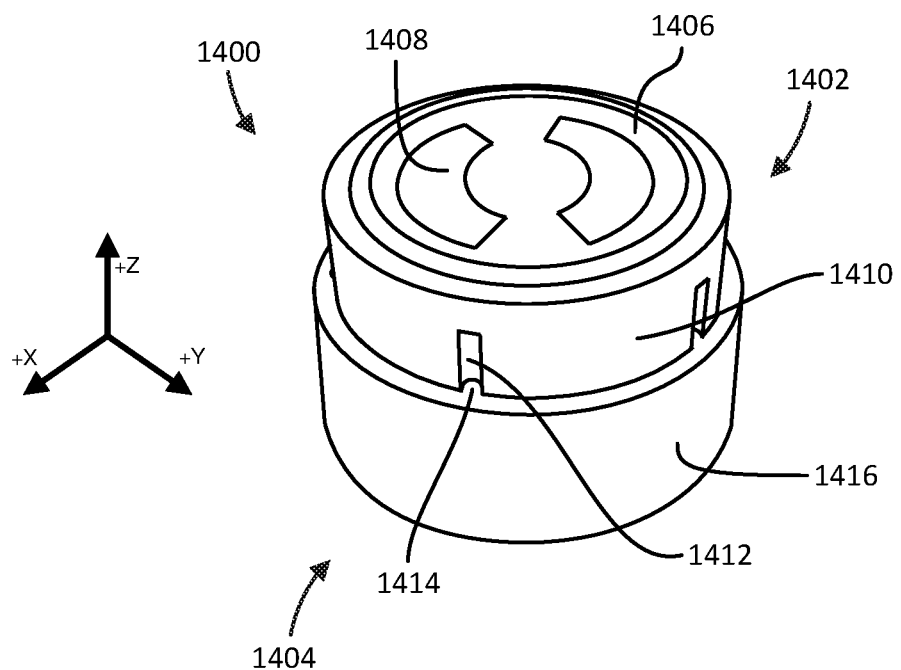

FIGS. 14A and 14B illustrate an exemplary compliant electrode 1400. As shown in these figures, compliant electrode 1400 may include a user-side component 1402 and a display-side component 1404. User-side component 1402 and display-side component 1404 may be constructed from any suitable material (e.g., plastic or aluminum). In some examples, display-side component 1404 may be coupled to or integrated within a frame or housing of a head-mounted-display device. As such, movement of display-side component 1404 may be restricted relative to the head-mounted display device. As shown in FIGS. 14A and 14B, user-side component 1402 may be configured to freely move in the illustrated Z direction (e.g., a direction normal to the surface of a user's face) but resist motion in the illustrated X and Y directions (e.g., directions tangent to the surface of the user's face).

User-side component 1402 may include a top surface 1406 that may include one or more conductive elements 1408 for conducting biopotential signals generated by a user's body. Additionally, user-side component 1402 may include a tubular housing 1410 with integrated sockets 1412 that are mateable to guides 1414 of a tubular housing 1416 of display-side component 1404. In some examples, sockets 1412 and guides 1414 may enable, when engaged, user-side component 1402 of compliant electrode 1400 to freely move in the illustrated Z direction but resist motion in the illustrated X and Y directions. In some examples, compliant electrode 1400 may include a compliant element (e.g., a compliant foam or a spring) between user-side component 1402 and display-side component 1404 that is configured to apply a force against user-side component 1402 and display-side component 1404.

Figure 15A:
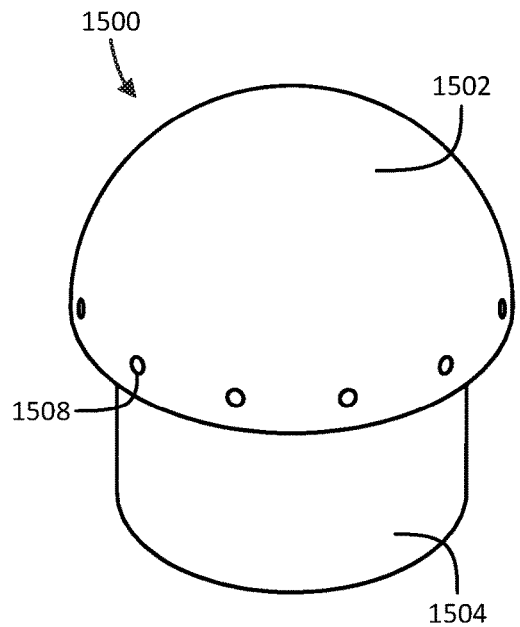
FIGS. 15A-15C are a perspective view, a side view, and a cross-sectional view of an additional exemplary compliant electrode in accordance with some embodiments.
Figure 15B:
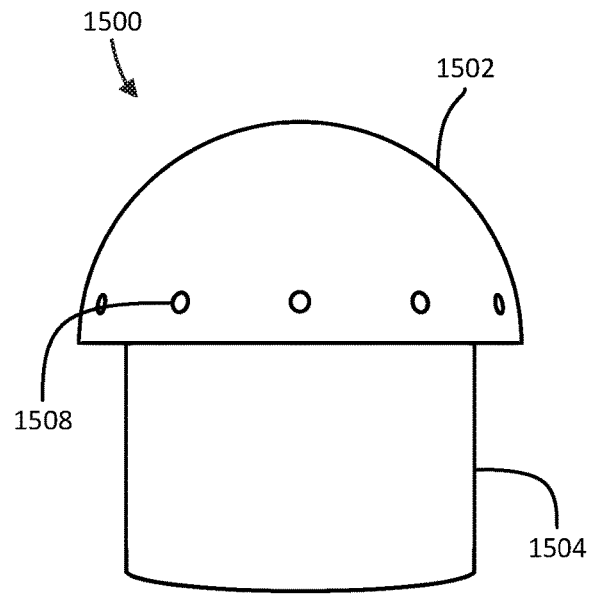
Figure 15C:
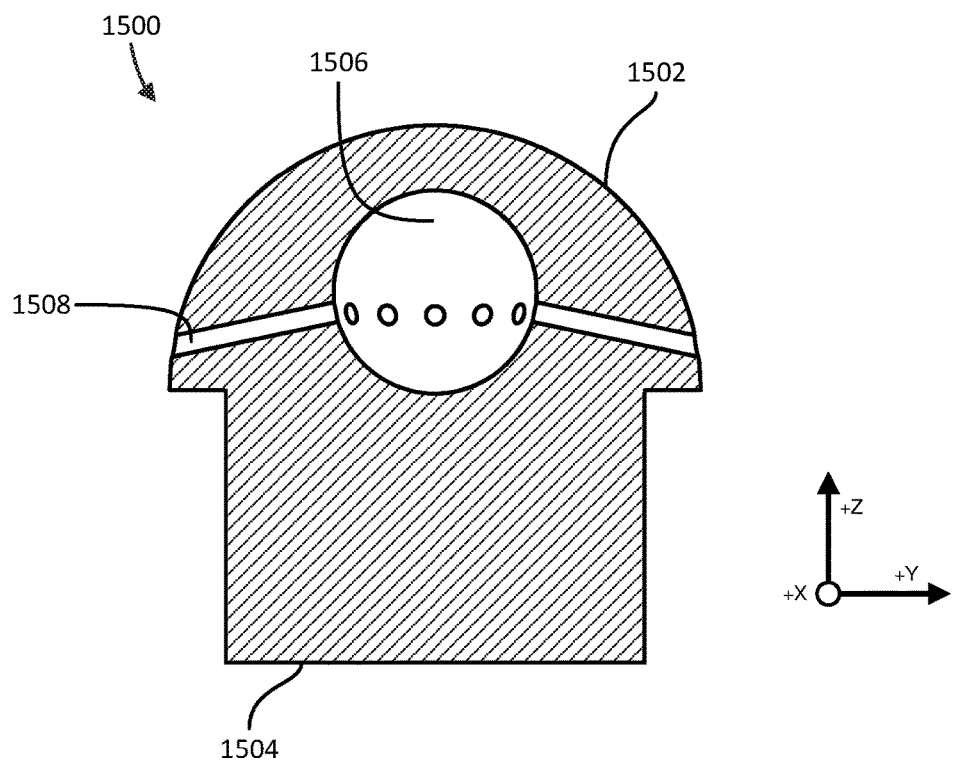

In some examples, compliant electrodes may be constructed from a suitable compliant conductive polymer. FIGS. 15A-15C illustrate an exemplary compliant contact electrode 1500. In some examples, compliant contact electrode 1500 may be constructed from a suitable compliant conductive polymer that is capable of conducting biopotential signals generated from a user's body. As shown in these figures, compliant electrode 1500 may include a spherical user-side surface 1502 configured to contact the user's body and a cylindrical display-side surface 1504 configured to interface with a head-mounted-display device. In some examples, display-side surface 1504 may be coupled to a frame or housing of a head-mounted-display device. As such, movement of exemplary compliant electrode 1500 may be restricted relative to the head-mounted display device (i.e., restricted relative to the illustrated X direction and the illustrated Y direction). As shown in FIGS. 15A-15C, exemplary compliant electrode 1500 may include a spherical void 1506 configured to enable user-side surface 1502 to be compressed in the illustrated Z direction (e.g., a direction normal to the surface of a user's face) but resist motion in the illustrated X and Y directions (e.g., directions tangent to the surface of the user's face). Exemplary compliant electrode 1500 may additionally include one or more openings 1508 configured to enable air to flow to and from void 1506.

Figure 16:
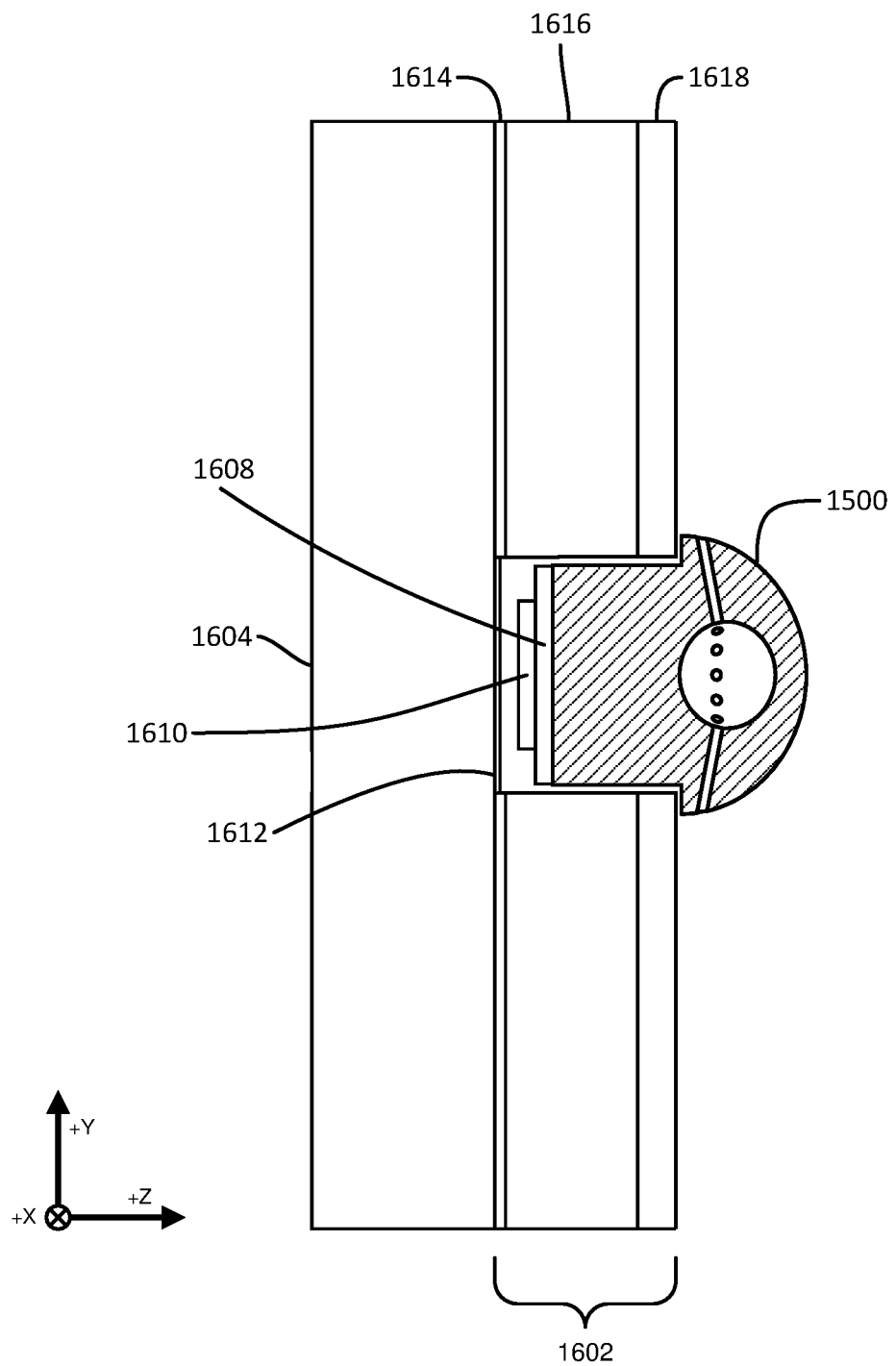
FIG. 16 is a cross-sectional view of an additional exemplary electrode configuration in accordance with some embodiments.

FIG. 16 shows an exemplary configuration in which compliant contact electrode 1500 may be integrated into a portion of a facial-interface subsystem 1602, which is attached to a frame 1604 of a head-mounted display. As shown in this example, compliant contact electrode 1500 may be coupled to a rigid board 1608 (e.g., a printed circuit board) that electrically couples compliant contact electrode 1500 to signal-receiving circuitry 1610 (e.g., analog conditioning circuits, amplifiers, capacitors, resistors, etc.). In this example, non-contact electrode 1500 may be aligned with a shielding layer 1612 (e.g., copper tape or a conductive coating) coupled to frame 1604 and configured to provide shielding for signal-receiving circuitry 1610.

As shown in FIG. 16, facial-interface subsystem 1602 may include a shielding layer 1614 (e.g., copper tape or a conductive coating), a compliant layer 1616, and a compliant layer 1618. Compliant layers 1616 and 1618 may each be made of any suitable compliant material. For example, compliant layers 1616 and 1618 may each be made of a compliant foam with a suitable thickness and stiffness. In some examples, compliant layer 1616 may be made of a compliant foam whose stiffness is equal to $k_1$, and compliant layer 1618 may be made of a compliant foam whose stiffness is equal to $k_2$. In at least one example, $k_2 > k_1$.

Figure 17C:
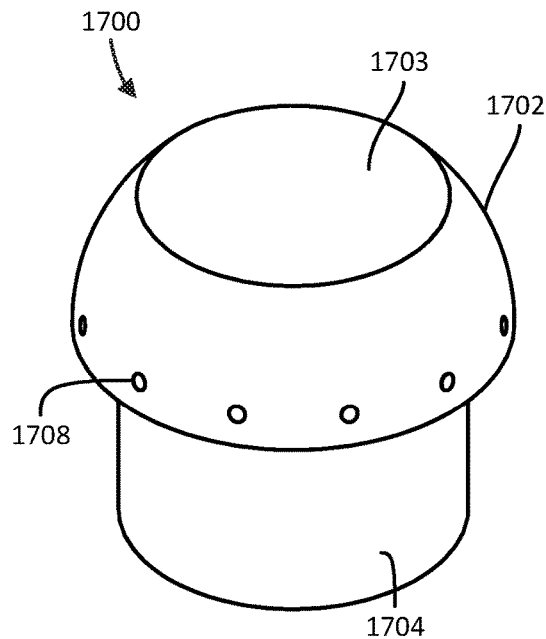
Figure 17C:
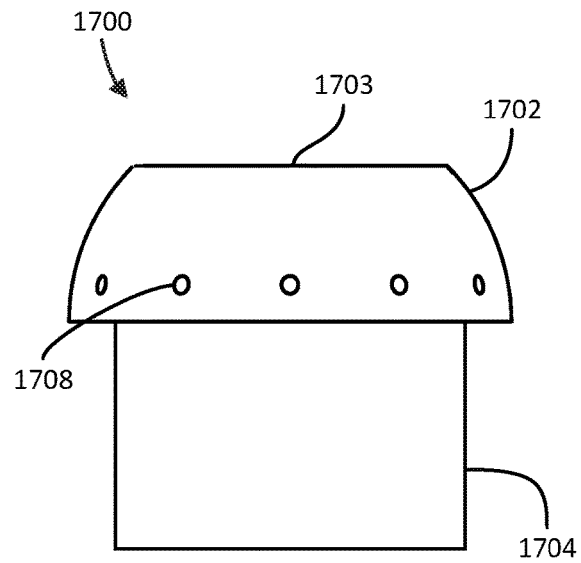
Figure 17C:
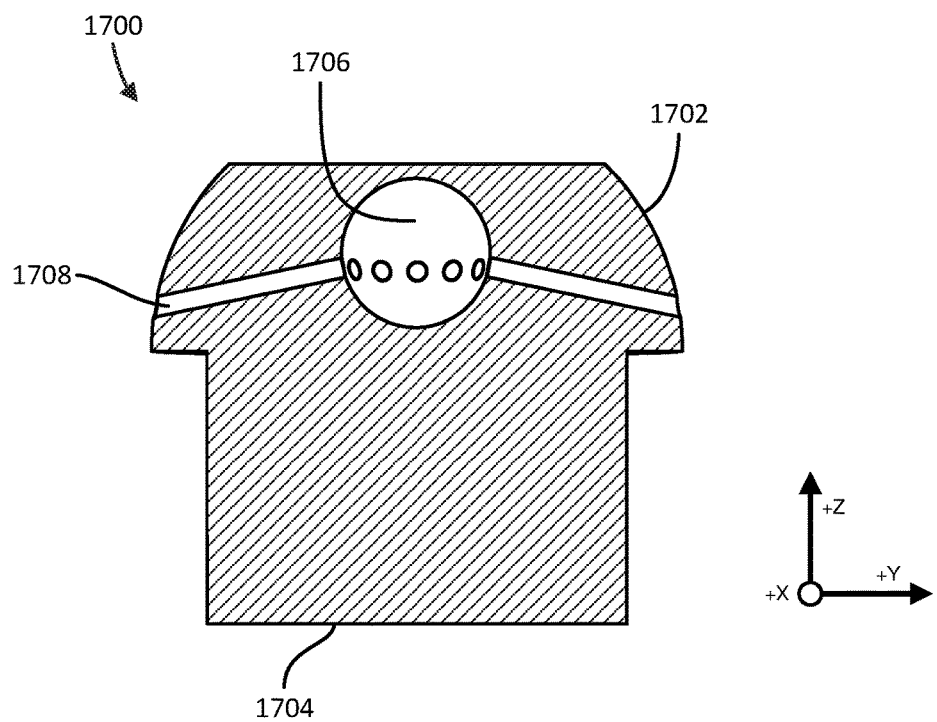

FIGS. 17A-17C illustrate an exemplary compliant electrode 1700. In some examples, compliant electrode 1700 may be constructed from a suitable compliant conductive polymer that is capable of conducting biopotential signals generated from a user's body. As shown in these figures, compliant electrode 1700 may include a spherical user-side surface 1702 with a flat surface 1703 configured to contact the user's body and a cylindrical display-side surface 1704 configured to interface with a head-mounted-display device. In some examples, display-side surface 1704 may be coupled to a frame or housing of a head-mounted-display device. As such, movement of exemplary compliant electrode 1700 may be restricted relative to the head-mounted display device. As shown in FIGS. 17A-17C, exemplary compliant electrode 1700 may include a spherical void 1706 configured to enable user-side surface 1702 to be compressed in the illustrated Z direction (e.g., a direction normal to the surface of a user's face) but resist motion in the illustrated X and Y directions (e.g., directions tangent to the surface of the user's face). Exemplary compliant electrode 1700 may additionally include one or more openings 1708 configured to enable air to flow to and from void 1706.

FIGS. 18A-18C illustrate an exemplary compliant electrode 1800. In some examples, compliant electrode 1800 may be constructed from a suitable compliant conductive polymer that is capable of conducting biopotential signals generated from a user's body. As shown in these figures, compliant electrode 1800 may include a spherical user-side surface 1802 with a plurality of flexible ripples 1803 configured to contact the user's body and a cylindrical display-side surface 1804 configured to interface with a head-mounted-display device. Flexible ripples 1803 may be configured with any suitable size or shape.

In some examples, display-side surface 1804 may be coupled to a frame or housing of a head-mounted-display device. As such, movement of exemplary compliant electrode 1800 may be restricted relative to the head-mounted display device. As shown in FIGS. 18A-18C, exemplary compliant electrode 1800 may include a spherical void 1806 configured to enable user-side surface 1802 to be compressed in the illustrated Z direction (e.g., a direction normal to the surface of a user's face) but resist motion in the illustrated X and Y directions (e.g., directions tangent to the surface of the user's face). Exemplary compliant electrode 1800 may additionally include one or more openings 1808 configured to enable air to flow to and from void 1806.

FIGS. 19A-19C illustrate various additional configurations for compliant electrodes made of conductive polymers. For example, FIG. 19A illustrates a compliant electrode 1900 having a cylindrical inner void 1902 and one or more additional cylindrical voids 1904 that radially extend from cylindrical inner void 1902 in a direction opposite a user-side surface 1906. FIG. 19B illustrates a compliant electrode 1910 having a cylindrical inner void 1912 and one or more additional cylindrical voids 1914 that radially extend from cylindrical inner void 1912. As shown in this figure, cylindrical voids 1914 may first extend radially from cylindrical inner void 1912 in a direction parallel to a user-side surface 1916 and may then extend towards user-side surface 1916. FIG. 19C illustrates a compliant electrode 1920 having a spherical user-side surface 1922 with flexible protrusions 1924 configured to contact a user's body. Exemplary compliant electrode 1920 may additionally include one or more openings 1926 configured to enable air to flow to and from a central void (not shown).

Figure 20:
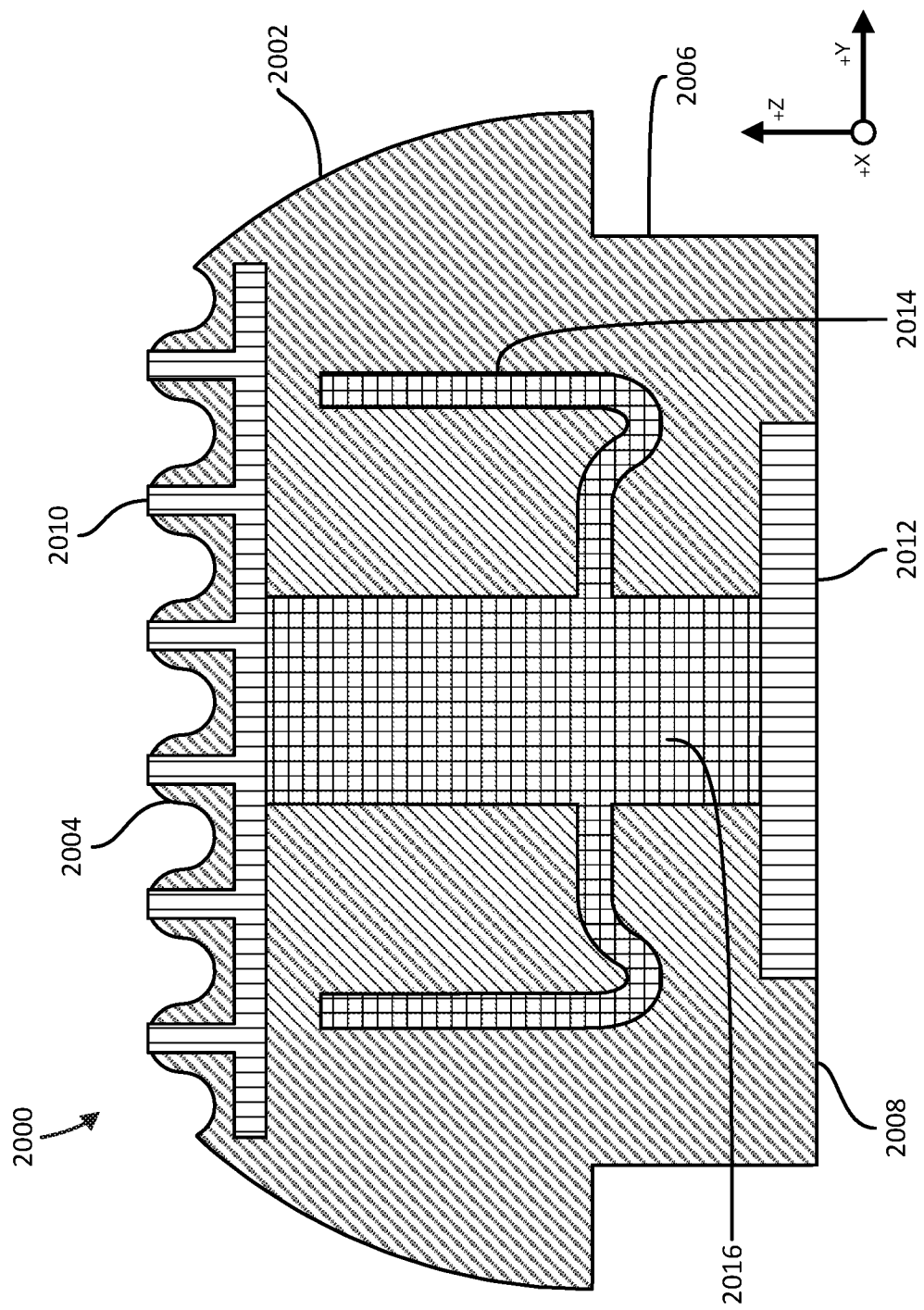
FIG. 20 is a cross-sectional view of an additional exemplary compliant electrode in accordance with some embodiments.

FIG. 20 illustrates an exemplary compliant electrode 2000. In some examples, compliant electrode 2000 may be constructed from a suitable compliant conductive polymer that is capable of conducting biopotential signals generated from a user's body. Alternatively, compliant electrode 2000 may be constructed from a suitable compliant non-conductive polymer. As shown in these figures, compliant electrode 2000 may include a spherical user-side surface 2002 with a rippled top 2004 configured to contact the user's body and a cylindrical display-side surface 2006 with a flat bottom 2008 configured to interface with a head-mounted-display device. As shown, spherical user-side surface 2002 may include a rigid metallic conductor 2010 protruding from rippled top 2004, and display-side surface 2006 may include a rigid metallic conductor 2012 integrated into flat bottom 2008.

In some examples, display-side surface 2006 may be coupled to a frame or housing of a head-mounted-display device. As such, movement of exemplary compliant electrode 2000 may be restricted relative to the head-mounted display device. As shown in FIG. 20, exemplary compliant electrode 2000 may include a void 2014 configured to enable user-side surface 2002 to be compressed in the illustrated Z direction (e.g., a direction normal to the surface of a user's face) but resist motion in the illustrated X and Y directions (e.g., directions tangent to the surface of the user's face). In some examples, void 2014 may be filled with a conductive liquid 2016 (e.g., a conductive gel) configured to electrically couple metallic conductor 2010 to metallic conductor 2012 when compliant electrode 2000 is compressed.

Figure 21:
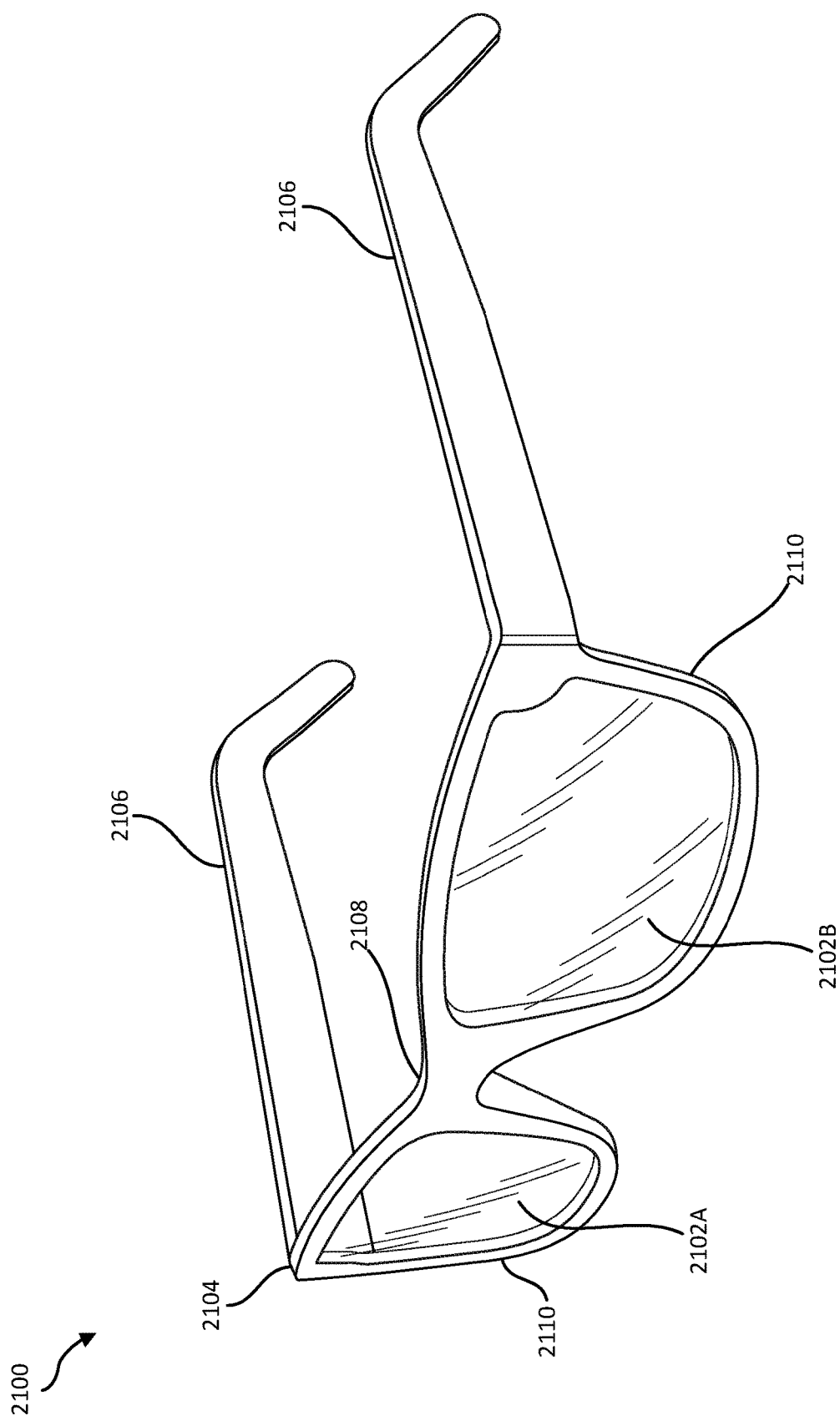
FIG. 21 is a perspective view of an exemplary head-mounted-display device in accordance with some embodiments.
Figure 22:
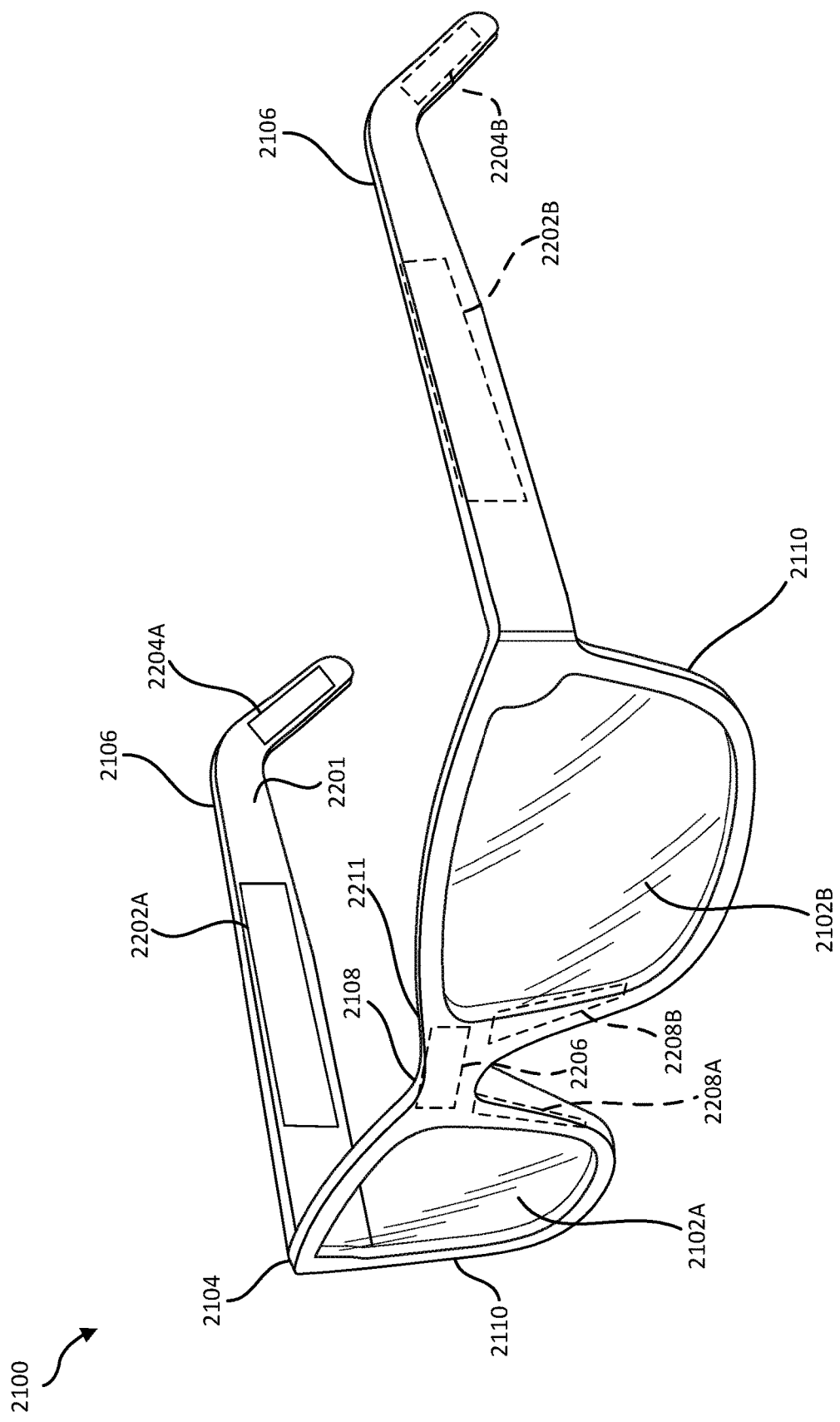
FIG. 22 is a perspective view of exemplary electrodes of the exemplary head-mounted-display device illustrated in FIG. 21 in accordance with some embodiments.

FIGS. 21 and 22 are diagrams of a head-mounted-display device 2100 according to some embodiments. The depicted embodiment includes a right near-eye display 2102A and a left near-eye display 2102B, which are collectively referred to as near-eye displays 2102. Near-eye displays 2102 may be transparent or semi-transparent lenses that include or utilize a display system (e.g., a projection display system) to present media to a user. Examples of media presented by near-eye displays 2102 include one or more images, a series of images (e.g., a video), audio, or some combination thereof. Near-eye displays 2102 may be configured to operate as an AR near-eye display, such that a user can see media projected by near-eye displays 2102 and see the real-world environment through near-eye displays 2102. However, in some embodiments, near-eye displays 2102 may be modified to also operate as VR near-eye displays, MR near-eye displays, or some combination thereof. Accordingly, in some embodiments, near-eye displays 2102 may augment views of a physical, real-world environment with computer-generated elements (e.g., images, video, sound, etc.).

As shown in FIG. 21, head-mounted-display device 2100 may include a support or frame 2104 that secures near-eye displays 2102 in place on the head of a user, in embodiments in which near-eye displays 2102 includes separate left and right displays. In some embodiments, frame 2104 may be a frame of eye-wear glasses. Frame 2104 may include temples 2106 configured to rest on the top of and/or behind a user's ears, a bridge 2108 configured to rest on the top on the bridge of the user's nose, and rims 2110 sized and configured to rest on or against the user's cheeks. Although not illustrated in FIG. 21, in some embodiments, head-mounted-display device 2100 may include nose pads for resting on the bridge of the user's nose. Head-mounted-display device 2100 may additionally or alternatively include various other features and/or components, including, for example, directional speakers to provide audio to a user, bone conduction transducers for providing sound signals to a user via vibrational bone conduction in an auditory region of the user's head, tracking and/or recording cameras, passive and/or active front and/or rear facing cameras to capture images from the user's environment, eye tracking cameras, ambient light, night vision, and/or thermal imaging sensors, multi-mode connectivity antennas for wireless communication, audio microphones for capturing sound in the user's environment, lights for illuminating a user's environment, inertial, haptic, environmental, and/or health monitoring sensors, and/or any other suitable components, without limitation.

Conductive elements, such as compliant electrodes, for receiving biopotential signals generated by a user's body may be incorporated into head-mounted-display device 2100 at various locations. FIG. 22 illustrates exemplary placements of compliant electrodes for head-mounted-display device 2100. In this example, a medial surface 2201 of one or both of temples 2106 may include compliant electrodes 2202 positioned, for example, to rest against or near the temple region of a user's face or against or near the region of a user's head above the user's ear and/or compliant electrodes 2204 positioned against or near the region of a user's head behind the user's ear. In some examples, a medial surface 2211 of bridge 2108 may include a compliant electrode 2206 configured to rest on or near the top of the user's nose and/or compliant electrodes 2208 configured to rest on or near the sides of a bridge of the user's nose. Although not shown, in at least one example, a medial surface of rims 2110 may include compliant electrodes configured to rest against or near the user's cheeks and/or portions of the user's face surrounding the user's eyes. In embodiments where head-mounted-display device 2100 has nose pads, some or all of the nose pads may also include compliant electrodes.

The compliant electrodes illustrated in FIG. 22 may be used to receive biopotential signals generated by a user's body in a variety of ways. In some examples, one or more of compliant electrodes 2202-2208 may act as a reference or ground electrode. In one example, compliant electrode 2206 may be used as a reference electrode. In some examples, all or some of compliant electrodes 2202-2208 may be used for EOG sensing. Additionally or alternatively, some or all of compliant electrodes 2202-2208 may be used for EMG sensing. For example, compliant electrodes 2202 and 2204 may be used to sense EMG signals generated when a user moves or clenches the user's jaw and/or moves the user's tongue. In another example, compliant electrodes 2202 and 2208 may be used to sense EMG signals generated by muscles near and around the user's eyes.

Figure 23:
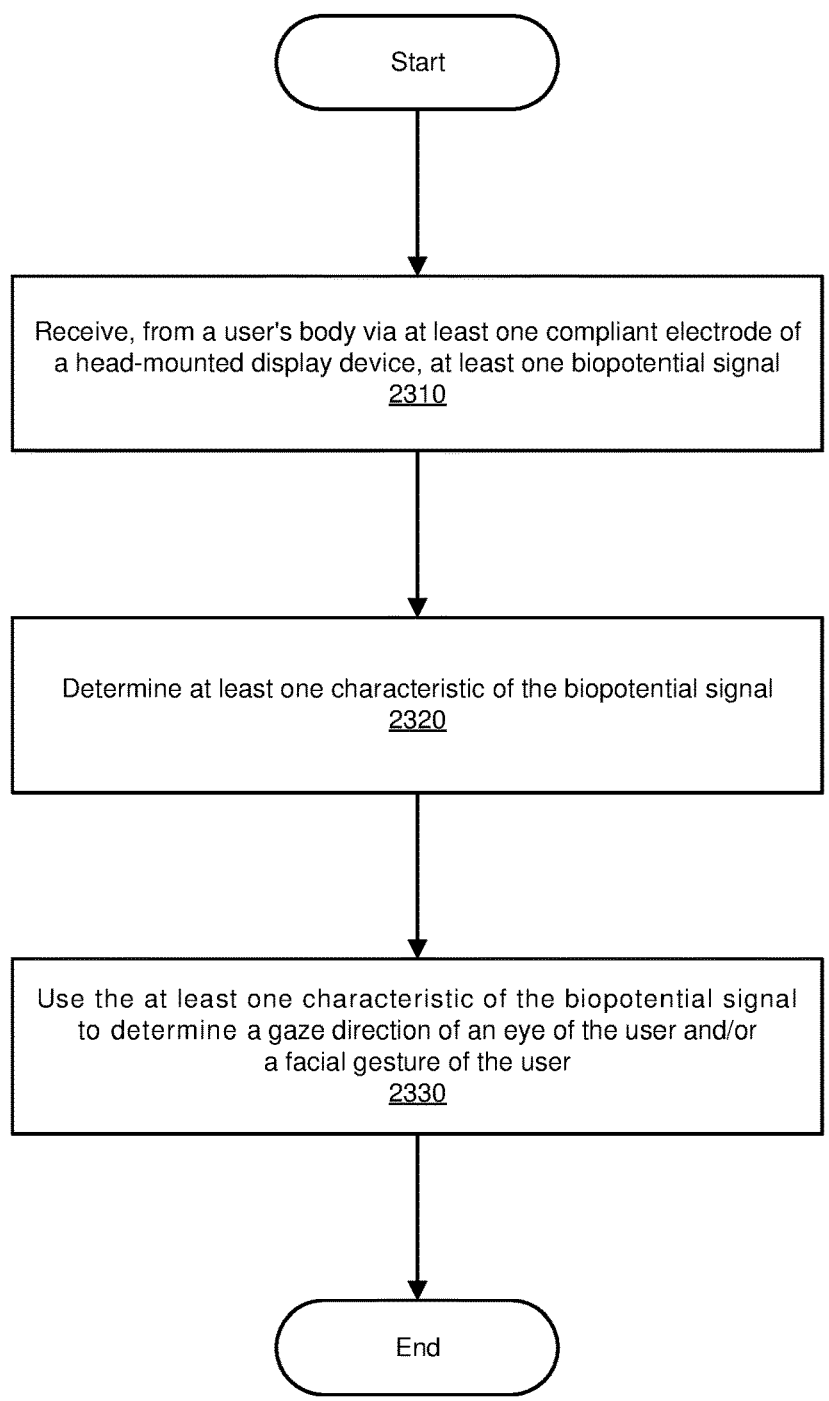
FIG. 23 is a flow diagram of an exemplary method for facilitating user interaction with an electronic device in accordance with some embodiments.

FIG. 23 is a flow diagram of an exemplary computer-implemented method 2300 for facilitating user interaction with electronic devices or other users according to some embodiments. The steps shown in FIG. 23 may be performed by any suitable computer-executable code and/or computing system, including the devices illustrated in FIGS. 3-22. In one example, each of the steps shown in FIG. 23 may represent an algorithm whose structure includes and/or is represented by multiple sub-steps, examples of which will be provided in greater detail below.

As illustrated in FIG. 23, at step 2310 one or more of the systems described herein may receive, from a user's body via at least one compliant electrode of a head-mounted display device, at least one biopotential signal. For example, receiving subsystem 310 shown in FIG. 3 may galvanically receive, from the body of user 302 via compliant electrodes 320 and 322 of facial coupling subsystem 318, one or more biopotential signals. In another example, receiving subsystem 410 shown in FIG. 4 may capacitively receive, from the body of user 402 via compliant electrodes 420-424 of facial coupling subsystem 418, one or more biopotential signals.

As illustrated in FIG. 23, at step 2320 one or more of the systems described herein may determine at least one characteristic of the biopotential signal. For example, detection subsystem 304 shown in FIG. 3 may determine at least one characteristic of the biopotential signal. In another example, detection subsystem 404 shown in FIG. 4 may determine at least one characteristic of the biopotential signal. In at least one example, the at least one characteristic of the biopotential signal may include at least one of a propagation delay of the biopotential signal, a magnitude of the biopotential signal, a phase of the biopotential signal, and/or a change to any one of these characteristics.

As illustrated in FIG. 23, at step 2330 one or more of the systems described herein may use the at least one characteristic of the biopotential signal to determine a gaze direction of an eye of the user and/or a facial gesture of the user. For example, gaze-detection subsystem 306 shown in FIG. 3 may use at least one characteristic of a biopotential signal generated by an eye of user 302 to identify a gaze direction of user 302. In another example, gesture-detection subsystem 308 shown in FIG. 3 may use at least one characteristic of a biopotential signal generated by a facial muscle of user 302 to identify a facial gesture of user 302.

FIGS. 24, 25A-25F, 26A-26F, and 27A-27C illustrate examples of various facial movements that may be detected by the disclosed systems. Such facial movements may be, for example, detected using a head-mounted-display device (see, e.g., FIGS. 5-22) having an array of compliant electrodes positioned abutting various regions of a user's face and/or other portions of the user's head using any of the techniques described herein. While a head-mounted-display device is not illustrated on the head of the user shown in FIGS. 24, 25A-25F, 26A-26F, and 27A-27C for ease in illustrating and visualizing the exemplary movements, such movements may be detected by a head-mounted-display device while the head-mounted-display device is worn on the user's head in the manner illustrated in, for example, FIGS. 5 and 6 with compliant electrodes of the head-mounted-display device abutting the user's head as shown, for example, in FIG. 10. While FIGS. 24, 25A-25F, 26A-26F, and 27A-27C show a number of exemplary facial movements that may be detected by a detection system (e.g., detection subsystem 304 and/or 404 shown in FIGS. 3 and 4) in conjunction with a head-mounted-display device, a detection system may be configured to additionally or alternatively detect any other suitable facial expressions, without limitation.

Figure 24:
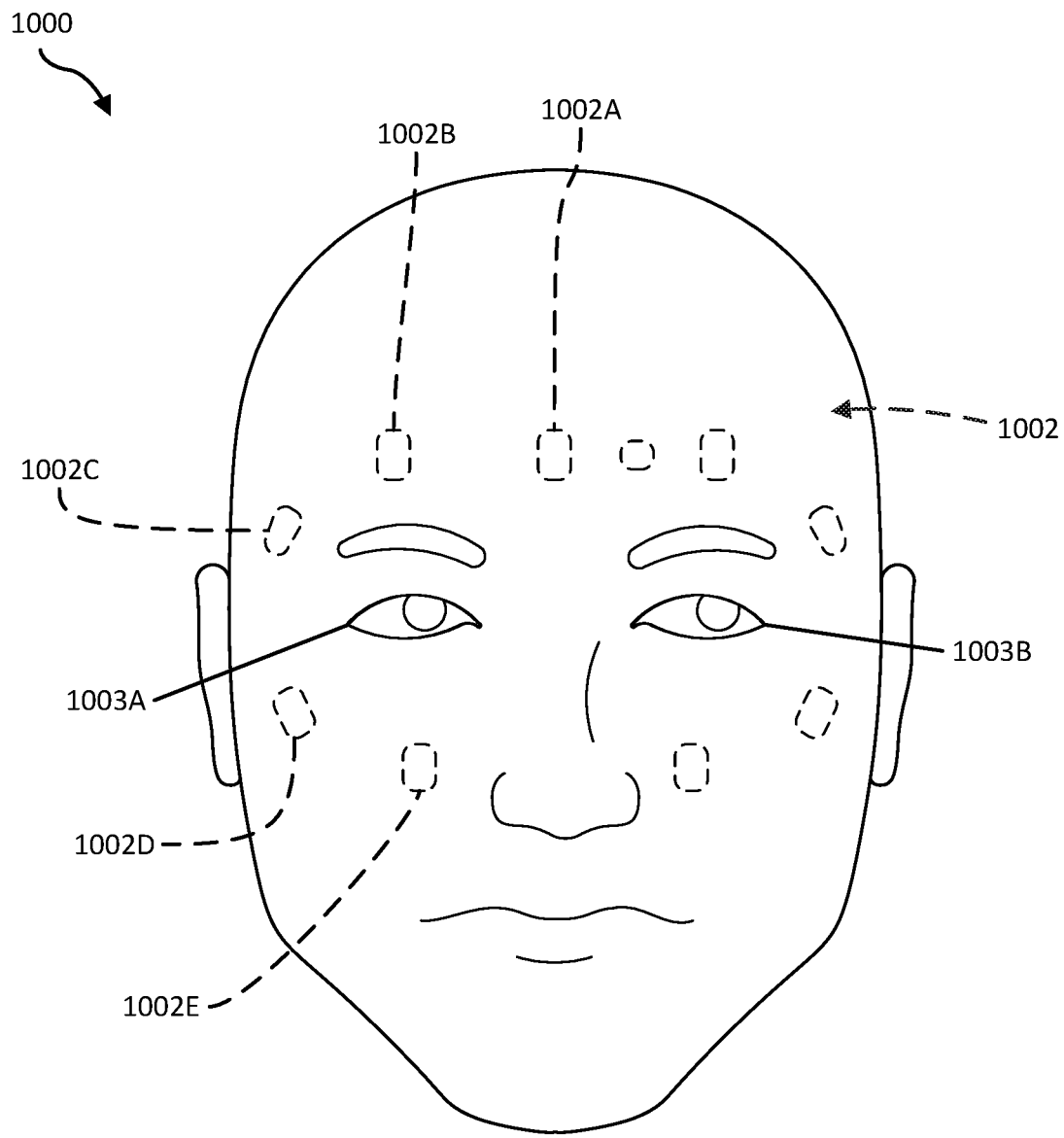
FIG. 24 is a view of the head of the user illustrated in FIG. 10 showing an exemplary change in a gaze direction of the user's eyes that may be detectable by a detection system in accordance with some embodiments.
Figure 25A:
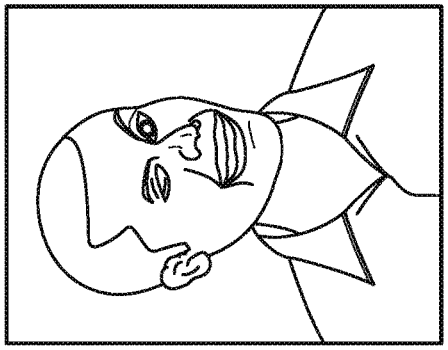
FIGS. 25A-25F are front views of exemplary facial expressions that may be detectable by a detection system in accordance with some embodiments.
Figure 25B:
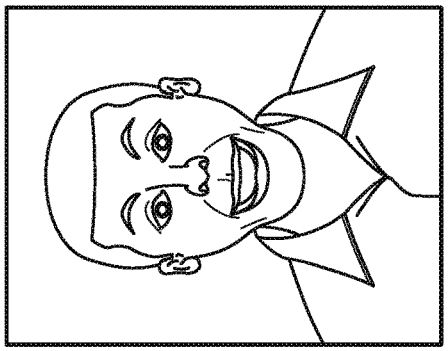

As discussed above in relation to FIG. 10, a disclosed detection system may detect facial movement in various regions of the user's face, head, and/or regions near the user's head (e.g., a neck region). As illustrated in FIGS. 10 and 24, the detection system may detect a shift in the gaze direction of the illustrated user's eyes 1003 (e.g., from straight ahead to looking left). As illustrated in FIG. 25A, the detection system may detect a user closing one eye in a winking gesture. Additionally or alternatively, the detection system may detect a user tilting their head and/or raising one cheek and/or one corner of their mouth as shown in FIG. 25A. As illustrated in FIG. 25B, the detection system may detect a user raising their eyebrows and/or smiling with corners of the mouth and cheeks raised, either with an open mouth, as shown, or with a closed mouth.

Figure 25C:
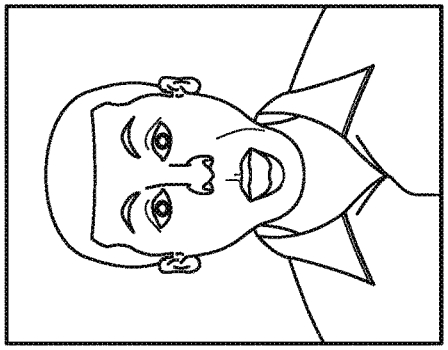
Figure 25D:
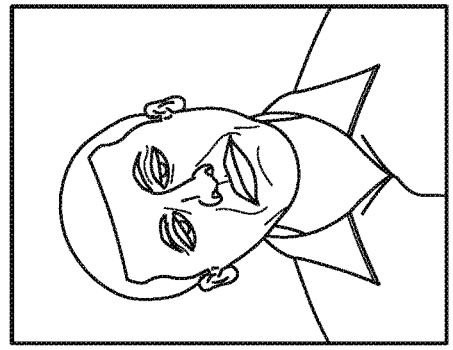
Figure 25E:
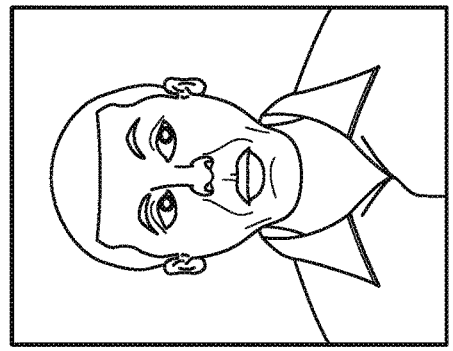
Figure 25F:
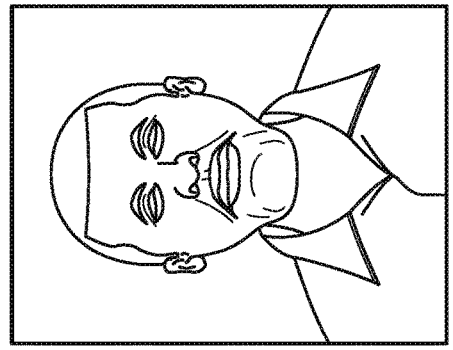

As illustrated in FIG. 25C, the detection system may detect a user raising their eyebrows and opening their mouth in, for example, an expression of surprise. As illustrated in FIG. 25D, the detection system may detect a user lowering their eyebrows, eyes, cheeks and/or corners of the mouth in, for example, an expression of sadness or dismay. Additionally or alternatively, the detection system may detect a user tilting their head as shown in FIG. 25D. As illustrated in FIG. 25E, the detection system may detect a user raising one eyebrow in, for example, an expression of curiosity or surprise. Additionally or alternatively, the detection system may detect a user moving their eyes to look in a sideward direction. As illustrated in FIG. 25F, the detection system may detect a user closing their eyes and/or lowering their cheeks and/or the corners of their mouth in an expression of, for example, disgust. Additionally or alternatively, the detection system may detect a user tilting their head backward as shown in FIG. 25F.

Figure 26C:
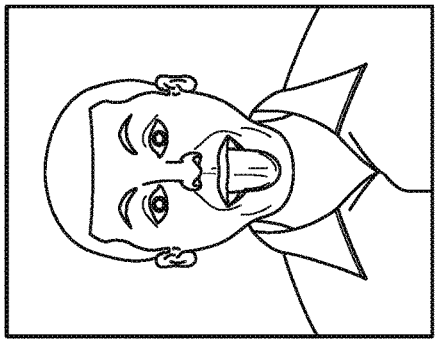
FIGS. 26A-26F are front views of additional exemplary facial expressions that may be detectable by a detection system in accordance with some embodiments.
Figure 26F:
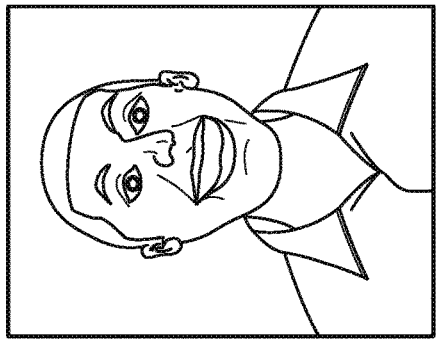
Figure 26B:
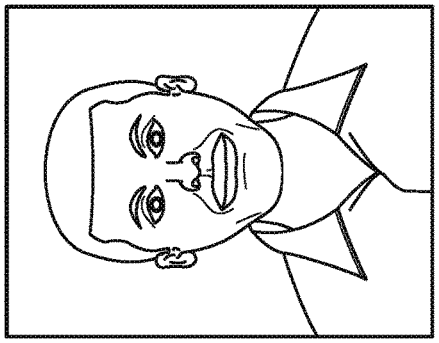
Figure 26E:
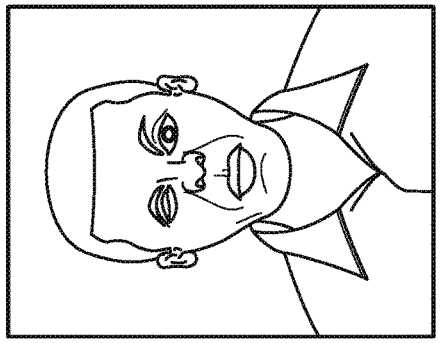
Figure 26A:
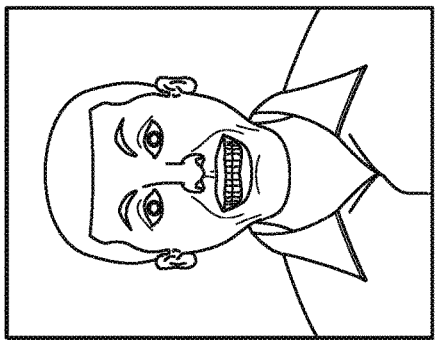
Figure 26D:
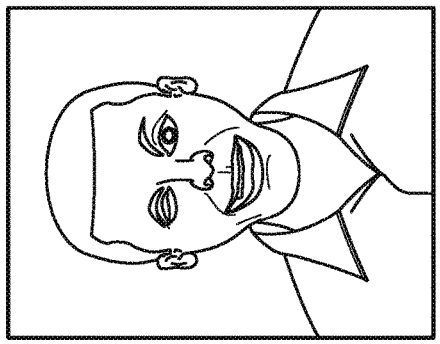

As illustrated in FIG. 26A, the detection system may detect a user raising their eyebrows and/or opening their mouth with closed teeth, with their cheeks and/or the corners of their mouth raised, in an expression of, for example, excitement or surprise. As illustrated in FIG. 26B, the detection system may detect a user with their mouth closed in, for example, a generally neutral expression. As illustrated in FIG. 26C, the detection system may detect a user making, for example, a humorous expression by sticking out their tongue and/or raising their eyebrows. As illustrated in FIG. 26D, the detection system may detect a user closing one eye, raising one eyebrow, raising one cheek, and/or raising one corner of their mouth. As illustrated in FIG. 26E, the detection system may detect a user closing one eye and raising one eyebrow while their mouth is closed and generally neutral.

Figure 27C:
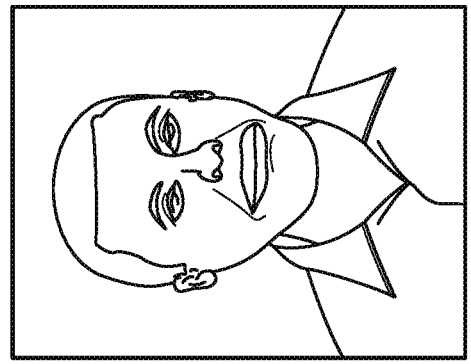
FIGS. 27A-27C are front views of additional exemplary facial expressions that may be detectable by a detection system in accordance with some embodiments.
Figure 27B:
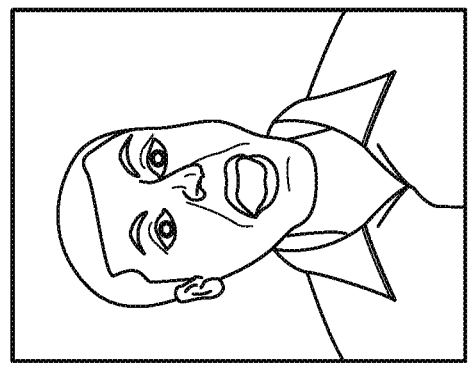
Figure 27A:
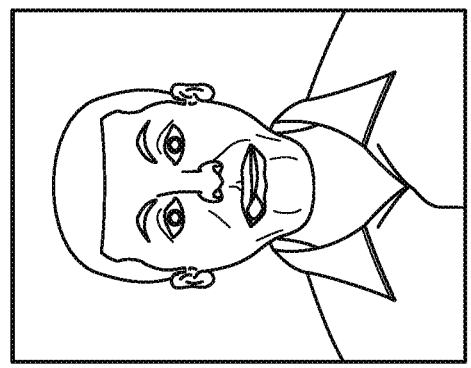

As illustrated in FIG. 26F, the detection system may detect a user with their mouth open in a wide smile, with their cheeks, the corners of their mouth, and/or their eyebrows raised in, for example, an excited expression. Additionally or alternatively, the detection system may detect a user tilting their head backward and to the side as shown in FIG. 26F. As illustrated in FIG. 27A, the detection system may detect a user raising their eyebrows and/or sticking out their tongue slightly from a side of their mouth. As illustrated in FIG. 27B, the detection system may detect a user raising their eyebrows and/or opening their mouth in, for example, an expression of shock or surprise. Additionally or alternatively, the detection system may detect a user tilting their head backward and to the side as shown in FIG. 27B. As illustrated in FIG. 27C, the detection system may detect a user partially closing their eyes with their lips closed in, for example, a tired or frustrated expression.

In some embodiments, facial gestures, such as the facial movements shown in FIGS. 24, 25A-25F, 26A-26F, and 27A-27C and or any other suitable facial movements, may be identified by a detection system (e.g., detection subsystem 304 and/or 404 shown in FIGS. 3 and 4) and used as input for performing one or more functions. According to at least one embodiment, facial expressions detected by one or more of the systems and/or configurations disclosed herein may be utilized to facilitate user interaction with electronic devices and/or interaction between users of electronic devices. For example, a user may make a facial movement to interact with at least one visual, audio, and/or haptic element presented to the user by a head-mounted-display device. For example, a user may make an eye or other facial movement indicating a selection and/or other interaction with a displayed image element visible to the user via a display region of a head-mounted-display device. The detection subsystem may detect the eye or other facial movement and may send a signal indicating the selection and/or other interaction to the head-mounted-display device and/or to an external device other than the head-mounted-display device. In at least one example, the head-mounted-display device may modify visual, audio, and/or haptic elements presented to the user in response to the signal indicating the selection and/or other interaction. For example, the head-mounted-display device may include a display controller that modifies images displayed in a display region of the head-mounted-display device in response to the signal indicating the selection and/or other interaction.

In some embodiments, facial movements, such as the eye movements and facial expressions shown in FIGS. 24, 25A-25F, 26A-26F, and 27A-27C and/or any other suitable facial movements, detected by one or more of the systems and/or configurations disclosed herein may be utilized to facilitate interaction between a user and at least one other user. For example, a user may make a facial movement that is detected and utilized for driving a visual representation of the user, such as an avatar, for purposes of interaction with other users. For example, an eye movement and/or facial gesture of the user may be detected by the detection subsystem, which may send data indicating a change in the visual representation of the user to the head-mounted-display device and/or to an external device other than the head-mounted-display device. The data indicating the change in the visual representation of the user may be utilized by the head-mounted-display device and/or the external device to change the appearance of the visual representation of the user. For example, an avatar of the user may be modified to visually represent a gaze direction or a facial expression corresponding to a gaze direction or a detected facial gesture of the user. Such a visual representation of the user may, for example, be visible to the user via a display region of the head-mounted-display device and/or may be visible to one or more other remote users via at least one display device visible to the other or more other remote users, thereby facilitating interaction between the user and the one or more other remote users.

As explained above, embodiments of the instant disclosure may enable a head-mounted device, such as a head-mounted display, with integrated compliant electrodes to harness biopotential signals generated by a wearer's body to detect the wearer's facial movements. By using compliant electrodes that comply in a direction normal to a wearer's face while restricting motion in any direction tangent to the wearer's face, embodiments of the instant disclosure may accurately and reliably measure biopotential signals generated by the wearer's body in a way that is also comfortable to the wearer.

In some examples, by accurately and reliably monitoring biopotential signals generated by a wearer's facial muscles and/or eyes, embodiments of the instant disclosure may enable devices to track the wearer's facial gestures and/or gaze direction based on changes in various characteristics of these biopotential signals. Such apparatus, systems, and methods may enable user interaction with electronic devices, such as head-mounted displays, without requiring users to input operations via conventional input interfaces, such as keyboards, controllers, headset buttons, voice-command interfaces, etc. Detection of user facial movements using biopotential-signal sensing may require less energy than conventional optical methods, thereby reducing power use and extending the life of battery-operated devices. Moreover, users may easily and efficiently convey facial movements to other remote users via such apparatus, systems, and methods. Accordingly, users may interact with electronic devices and other users in a manner that provides a broader range of interactive capabilities while facilitating a greater sense of immersion in VR and AR environments.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the subsystems and/or modules described herein may transform data, physical devices, and/or representations of physical devices from one form to another. For example, one or more of the subsystems and/or modules recited herein may receive a biopotential signal generated by a human body via a compliant electrode, transform the biopotential signal into a correlated result for determination of a facial movement, output a result of the transformation to one or more electronic devices, use the result of the transformation to modify a displayed image, and/or store the result of the transformation. Additionally or alternatively, one or more of the subsystems and/or modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

Embodiments of the instant disclosure may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the instant disclosure. The embodiments disclosed herein should be considered in all respects illustrative and not restrictive. Reference should be made to the appended claims and their equivalents in determining the scope of the instant disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. An interactive system comprising:
   a facial coupling subsystem configured to conduct at least one biopotential signal generated by a user's body, the facial coupling subsystem comprising:
   a compliant cushion layer comprising:
      a user-side surface dimensioned to abut a facial portion of the user; and
      a display-side surface dimensioned to abut a mounting surface of a head-mounted device; and
   a plurality of compliant electrodes, wherein:
      each of the plurality of compliant electrodes comprises an interface mateable to an opposing interface of the mounting surface of the head-mounted device; and
      the interface of each of the plurality of compliant electrodes is configured to allow the compliant electrode to move in a direction normal to the surface of the user's face and substantially prevent the compliant electrode from moving in any direction tangent to the surface of the user's face;
   a receiving subsystem electrically connected to the facial coupling subsystem and configured to receive, from the user's body via at least one compliant electrode of the facial coupling subsystem, the biopotential signal; and
   a detection subsystem electrically connected to the receiving subsystem and configured to:
      determine at least one characteristic of the biopotential signal; and
      use the at least one characteristic of the biopotential signal to determine at least one of:
         a gaze direction of an eye of the user; or
         a facial gesture of the user.

2. The interactive system of claim 1, wherein each of the plurality of compliant electrodes is positioned beneath the user-side surface.

3. The interactive system of claim 1, wherein each of the plurality of compliant electrodes comprises a user-side surface comprising a plurality of flexible protrusions.

4. The interactive system of claim 1, wherein the interface of each of the plurality of compliant electrodes comprises a plurality of legs, each of the plurality of legs mateable to an opposing socket of the mounting surface of the head-mounted device.

5. The interactive system of claim 1, wherein the interface of each of the plurality of compliant electrodes comprises a plurality of sockets, each of the plurality of sockets mateable to an opposing leg of the mounting surface of the head-mounted device.

6. The interactive system of claim 1, wherein the interface of each of the plurality of compliant electrodes comprises a tubular housing mateable to an opposing tubular socket of the mounting surface of the head-mounted device.

7. The interactive system of claim 1, wherein each of the plurality of compliant electrodes comprises compliant foam configured to apply a force against the compliant electrode and the mounting surface of the head-mounted device when the compliant electrode is compressed by the surface of the user's face.

8. The interactive system of claim 1, wherein each of the plurality of compliant electrodes comprises a spring configured to apply a force against the compliant electrode and the mounting surface of the head-mounted device when the compliant electrode is compressed by the surface of the user's face.

9. The interactive system of claim 1, wherein each of the plurality of compliant electrodes is composed of a single piece of conductive polymer.

10. The interactive system of claim 9, wherein the single piece of conductive polymer comprises a hollow center configured to enable the single piece of conductive polymer to comply in the direction normal to the surface of the user's face and substantially resist motion in any direction tangent to the surface of the user's face.

11. The interactive system of claim 10, wherein the single piece of conductive polymer comprises a plurality of openings configured to enable air to flow to and from the hollow center.

12. The interactive system of claim 10, wherein:
   the single piece of conductive polymer comprises:
      a user-side surface comprising a first rigid metallic conductor configured to contact the surface of the user's face; and
      a display-side surface comprising a second rigid metallic conductor configured to conduct the biopotential signal to electronic components of the head-mounted device; and
   the hollow center is filled by a conductive liquid that electrically connects the first rigid metallic conductor to the second rigid metallic conductor.

13. The interactive system of claim 9, wherein the single piece of conductive polymer comprises a spherical user-side surface.

14. The interactive system of claim 9, wherein the single piece of conductive polymer comprises a flat user-side surface.

15. The interactive system of claim 9, wherein the single piece of conductive polymer comprises a user-side surface, the user-side surface comprising a plurality of ridges.

16. The interactive system of claim 9, wherein the single piece of conductive polymer comprises a user-side surface, the user-side surface comprising a plurality of equally spaced protrusions.

17. The interactive system of claim 1, further comprising a communication subsystem configured to transmit data to an external device, wherein the communication subsystem is configured to modify the data transmitted to the external device based on the gaze direction or the facial gesture.

18. A head-mounted-display device comprising:
a facial coupling subsystem configured to conduct at least one biopotential signal generated by a user's body, the facial coupling subsystem comprising:
a compliant cushion layer comprising:
a user-side surface dimensioned to abut a facial portion of the user; and
a display-side surface dimensioned to abut a mounting surface of the head-mounted display device; and
a plurality of compliant electrodes, wherein:
each of the plurality of compliant electrodes comprises an interface mateable to an opposing interface of the mounting surface of the head-mounted display device; and
the interface of each of the plurality of compliant electrodes is configured to allow the compliant electrode to move in a direction normal to the surface of the user's face and substantially prevent the compliant electrode from moving in any direction tangent to the surface of the user's face;
a receiving subsystem electrically connected to the facial coupling subsystem and configured to receive, from the user's body via at least one compliant electrode of the facial coupling subsystem, the biopotential signal; and
a detection subsystem electrically connected to the receiving subsystem and configured to:
determine at least one characteristic of the biopotential signal; and
use the at least one characteristic of the biopotential signal to determine at least one of:
a gaze direction of an eye of the user; or
a facial gesture of the user.

19. The head-mounted-display device of claim 18, further comprising:
a display region configured to display images to the user; and
a display controller configured to modify the images displayed in the display region based on the gaze direction of the user's eye or the facial gesture of the user.

20. A method comprising:
receiving, from a user's body via at least one compliant electrode of a facial coupling subsystem of a head-mounted display device, at least one biopotential signal, wherein:
the facial coupling subsystem comprises:
a compliant cushion layer comprising:
a user-side surface dimensioned to abut a facial portion of the user; and
a display-side surface dimensioned to abut a mounting surface of the head-mounted display device; and
the at least one compliant electrode;
the at least one compliant electrode comprises an interface mateable to an opposing interface of a mounting surface of the head-mounted display device;
the interface of the at least one compliant electrodes is configured to allow the at least one compliant electrode to move in a direction normal to the surface of the user's face and substantially prevent the at least one compliant electrode from moving in any direction tangent to the surface of the user's face; and
the biopotential signal was generated by at least one of:
a corneo-retinal electric potential that exists between a front and a back of the user's eye; or
an electric potential of a muscle of the user;
determining at least one characteristic of the biopotential signal; and
using the at least one characteristic of the biopotential signal to determine at least one of:
a gaze direction of an eye of the user; or
a facial gesture of the user.

* * * * *